(12) United States Patent
Yamada et al.

(10) Patent No.: US 6,197,774 B1
(45) Date of Patent: Mar. 6, 2001

(54) PYRIMIDINE DERIVATIVE

(75) Inventors: Satoshi Yamada, Otsu; Naosumi Kinoshita, Kusatsu; Koichi Yasumura, Otsu; Kouji Edamatsu, Otsu; Takao Nagahama, Otsu; Shintaro Ishikawa, Otsu; Takeshi Yamauchi, Kyoto; Kazumasa Kishi, Kurita-gun; Kazuhisa Sugiyama, Otsu, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/380,742
(22) PCT Filed: Mar. 12, 1998
(86) PCT No.: PCT/JP98/01042
 § 371 Date: Sep. 13, 1999
 § 102(e) Date: Sep. 13, 1999
(87) PCT Pub. No.: WO98/41526
 PCT Pub. Date: Sep. 24, 1998

(30) Foreign Application Priority Data

Mar. 14, 1997 (JP) .................................................. 9-061550

(51) Int. Cl.⁷ ..................... C07D 487/04; A61K 31/505; A61P 11/06; A61P 37/08
(52) U.S. Cl. ........................................... 514/258; 544/281
(58) Field of Search .............................. 544/281; 514/258

(56) References Cited

U.S. PATENT DOCUMENTS 5,843,951  12/1998  Inooue et al. ..................... 514/258

FOREIGN PATENT DOCUMENTS 0 015 065    9/1980   (EP) .

OTHER PUBLICATIONS

Australian Official Action dated Apr. 17, 2000.

*Primary Examiner*—Mukund J. Shah
*Assistant Examiner*—Hong Liu
(74) *Attorney, Agent, or Firm*—Finnegan, Henderson, Farabow, Garrett & Dunner, L.L.P.

(57) ABSTRACT

The present invention provides a novel pyrimidine derivative represented by the general formula (1):

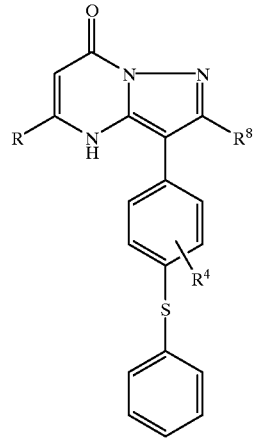

(1)

(wherein R, $R^4$ and $R^8$ are the same as defined in the specification) or pharmaceutically acceptable salt thereof, which possesses an excellent activity for inhibiting the formation of NO (nitrogen oxide) in vivo.

7 Claims, No Drawings

PYRIMIDINE DERIVATIVE

FIELD OF THE INVENTION

The present invention relates to a novel pyrimidine derivative which inhibits the formation of NO (nitrogen monoxide) in vivo, and relates to agents for curing asthma and atopic dermatis is containing, as the effective ingredient, said pyrimidine derivative or a salt thereof.

BACKGROUND ART

There have been known that NO (nitrogen monoxide) is generated in vivo when L-citrulline is formed by oxidation of the constitutional nitrogen atoms in the guanidino moiety of arginine through N-hydroxy-L-arginine intermediate. This reaction proceeds by action of NO synthase (hereinafter referred to as NOS) which acts as a catalyst.

There have been known several types of NOS, thus cNOS (constitutive NOS) which is constitutively existed naturally in the cells, and iNOS (inducible NOS) is synthesized inductively by stimulation of cytokaines or endotoxins [e.g., lipopolysaccharide (LPS)]. Examples of cNOS, includes endothelial cell NOS (eNOS) and nerve cell NOS (nNOS), and examples of iNOS includes macrophage NOS (mNOS).

Excessive amounts of NO and its metabolic products formed in vivo by the action of above-mentioned NOS (mainly, iNOS) induce several activities, such as lowering the blood pressure, activation of guanylate cyclase, acceleration of ribosylating adenosine diphosphate (ADP), deactivation of iron-containing enzymes, inhibition of synthesis of proteins and nucleic acids, inhibiting aggregation of platelet, inhibiting adhesion of neutrophil, etc., thus NO takes part in onset of various diseases.

For example, NO has an influence to disturb the native functions of the cells. Therefore, when a certain amount of NO is generated in the cells due to postponement of over-manifestation of iNOS, then it is understood that NO acts as a disturbance factor to the living body.

The disturbance factor is known to be regarded to various pathemas for example, septic shock, inflammations, reperfusion disturbance, arteriosclerosis, hypertension and myocarditis which may be occurred relating to the blood vessels and cardiac system; pneumonia and asthma which may be occurred relating to the lung and respiratory system; acute renal failure and glomerular philitis which may be occurred relating to the renal system; neurotoxicity, spasm, migraine, hyperesthesia which may be occurred relating to the brain and nervus system; mucosal disturbance, ulcerative colitis and diabetes mellitus which may be occurred relating to the digestive system; chronic rheumatic arthritis and the like which may be occurred relating to the immunological system.

Asthma is basically occurred due to spasmodic contraction of smooth muscle of the airway together with inflammation of the airway, deposition of viscous secreta inside of the airway, and edema of the airway mucosa.

There have been proposed several theories relating to pathogenesis of asthma, e.g., 1) mechanism based on allergy, 2) infections with microorganisms, 3) autonomic imbalance, 4) psychoneurotic cause, 5) β-blocking theory, 6) predisposing cause, 7) over response of the airway, 8) a specific mechanism, etc., and among of these theories the mechanism based on allergy is considered as the most important cause.

In asthmatic patients, there are two types of symptoms, one of them is an immediate asthmatic response (IAR) in which the asthmatic attack is induced quickly after the exposure to an antigen, another of them is a late asthmatic response (LAR) in which the asthmatic attack is manifested slowly thus, several hours after the exposure to an antigen. At present, an agent for inhibiting LAR is particularly desired.

Currently, β-stimulant drugs, steroidal anti-inflammatory drugs are mainly administered to asthmatic patients. However, there are reported that asthmatic patients are encountered in high risk to asthmatic death in case of administered β-stimulant drug in high dosage. As to the mechanism of side-effects of β-stimulant drug, the cardiac arrhythmia and drug tolerance are considered to be the highest possibility.

Additionally, steroidal anti-inflammatory drugs are indeed effective to cure asthmatic symptoms, while they bring serious systemic side-effects. Of cause, certain countermeasures are tried to reduce such side-effects caused by inhalation type of steroidal drugs. However, similar to oral administration type drugs, some dangers may be caused to osteoporosis and lowering of lung compliance by such inhalation type drugs. Thus, any drug being capable of replacing steroidal drugs, or any drug having the ability at least to reduce the dosage of the steroidal drugs are desired.

For the purpose to reduce dosage of steroidal drugs, there are reported that mild effects for reducing the dosage can be expected by using Methotrexate, a gold salt containing drug and cyclosporins. However, these drugs itself have severe side-effects which are different from the side-effects shown by the steroidal drugs. Thus, any drug without having these side-effects are desired.

On the other hand, although calcium antagonists may be used for reducing constriction of the airway, but they show much side-effects and are not practical. While by using PAF (platelet activating factor) antagonists, there was not reported any preferable results in curing asthmatic disease.

Under the circumstances, any drug being capable to substitute steroidal drugs or any drugs having similar effect to steroidal drugs without side-effect is desired. That is, any drug effective to patient who is suffering from the disease caused by tolerance to steroidal drug or vicious asthmatic disease such as asthma resistant to steroidal drug is desired.

It is known that amounts of NO and its derivatives in the exhalation of bronchial asthmatic patient is found to be increased.

Also, it is understood that NO is closely relates to the constriction of smooth muscle of the trachea together with inflammation of the airway, also relates to atopic dermatitis.

With respect to a pyrimidine derivative represented by the general formula (1) of the present invention, having inhibitory action against the effects of NO, the present inventors have made studies on anti-allergic activities, especially on anti-asthmatic effect and anti-atopic dermatitis effect performed thereby. As the result, the inventors have found the facts that, the pyrimidine derivative (1) of the present invention is a compound to be substituted for conventional steroidal drugs or a compound which is capable to reduce the dosage of conventional steroidal drugs, for this reason that the pyrimidine derivative (1) possesses activity for inhibiting the generation of NO, especially it performs an excellent effect for curing the late asthmatic response (LAR), also possesses an equivalent or higher performance in anti-asthmatic effect and anti-atopic dermatitis, as compared with the activity shown by conventional steroidal anti-inflammatory drug.

As to the NOS inhibitors to be used for curing the above-mentioned diseases, there are known, for example L-NMMA (N$^G$-monomethyl-L-arginine), L-NA (N$^G$-nitro-L-arginine), L-AME (L-arginine methyl ester), L-NAME (N$^G$-nitro-L-arginine methyl ester) and the like.

However, administration of these NOS inhitors cannot good enough for cure the above-mentioned various diseases. Under such circumstances, novel compounds having excellent activities for inhibiting the formation of NO in vivo and in case of curing asthma, an agent to be able to substitute for steroidal drugs, or an agent having at least effect for saving the dosage of steroidal drugs is desired.

In JP-A-5-112571, WO 97/11946, WO 95/35298 and JP-A-6-312987, there are disclosed pyrimidine derivatives similar to the pyrimidine derivatives (1) of the present invention. However, there are not any disclosure relating to the activity for inhibiting the formation of NO performed by these pyrimidine derivatives known in these prior art.

DISCLOSURE OF THE INVENTION

In consideration of the above-mentioned facts, the present inventors have made an extensive research work to solve the above-mentioned subjects. As the result, the present inventors have found the facts and knowledges that novel pyrimidine derivatives represented by the following general formula (1) and pharmaceutically acceptable salts thereof possess excellent effects for inhibiting the formation of NO, as well as having the effects for curing asthma and atopic dermatitis, and finally the present invention was successfully completed.

(1)

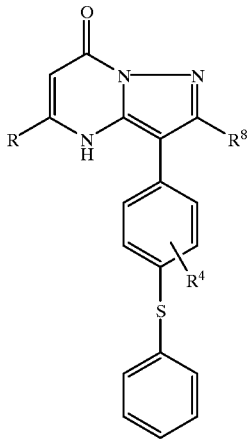

[wherein R represents a group of the formula:

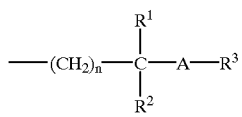

(wherein $R^1$ is a hydrogen atom or a lower alkyl group; $R^2$ is a hydrogen atom or a lower alkoxy group; $R^3$ is a hydrogen atom, an alkyl group, a lower alkanoyl group, a phenyl group which may have substituents selected from the group consisting of a lower alkoxy group, a carboxyl group, a halogen substituted-lower alkyl group and a lower alkyl group, an aralkyl group, a heterocyclic group, a cycloalkyl group, a hydroxy-lower alkyl group, and a lower alkoxy-lower alkyl group; A is an oxygen atom or sulfur atom; further $R^2$ and $R^3$ may be combined to each other to form 5- or 6-membered heterocyclic group; n is 0–2); $R^4$ is a hydrogen atom, a lower alkyl group or a lower alkoxy group; $R^8$ is a hydrogen atom, a lower alkyl group or a lower alkoxy-lower alkyl group].

In addition to the activity for inhibiting the generation of NO in vivo, the pyrimidine derivative (1) of the present invention possesses the activities for inhibiting the productions of mediators such as cytokines [e.g., IL-4, IL-5 and IL-8 (Interleukin-4, -5 and -8)], TNF-α (Tumor necrosis factor-α), LT (Leukotrienes), PAF (platelet-activating factor), PGs (prostaglandins), GM-CSF (granulocyte-macrophage colony-stimulating factor) and the activity for inhibiting 5-lipoxygenase, thus, the pyrimidine derivative (1) possesses excellent effects for curing various allergic diseases inflammatory diseases, and cancers.

Furthermore, the pyrimidine derivative (1) possesses permeability to the blood vessels of the airway, and having activity for inhibiting cellular infiltration into the alveolus, particularly it is excellent for curing bronchial asthma, inhibiting of the late asthmatic response in the bronchial asthma, and for curing vicious asthmatic diseases such as steroidal drug tolerated asthma, and, asthma resistant to steroidal drug, and for curing atopic dermatitis.

In the present invention, bronchial asthma, allergic rhinitis, atopic dermatitis and allergic dermatitis are exemplified as the allergic diseases.

The pyrimidine derivatives (1) of the present invention is characterized by having strong activities for inhibiting the formation of NO, having long acting time, good property of translocation in blood, and excellent effect of selectivity for the organs, further having low toxicity.

The pyrimidine derivative (1) of the present invention or pharmaceutically acceptable salts thereof have excellent activity for inhibiting the generation of NO in vivo. Therefore, the pyrimidine derivatives (1) can be used suitably for curing various diseases which are caused by excessive amounts of NO and its metabolic products. Examples of diseases are, arthritis, gastritis, glomerular philitis, ulcerative colitis, bronchitis, myocarditis, heart diseases, cardiac ishemia, ocular anemia, retinitis, uveitis, diabetes mellitus, septic shock, toxic shock, hypotension, neurogenic degeneration, gastrointestinal disturbances, sunburn, eczematoid dermatitis, psoriasis, adult respiratory distress syndrome (ARDS), atherosclerosis, systemic sclerosis, chronic sclerosis, multiple sclerosing degeneration, Crohn's disease, systemic lupus erythematodes, follicular fibrosis, hypoxia, spam and toxicity caused by hyperbaric oxygen, dementia, Sydenham's chorea, Huntington's disease, muscular atrophic disease, Korsakoff's disease, mental deterdation caused by megaroencephalia, cerebral cell injury and secondary diseases thereby, ishemic cerebral edema, schizophrenia, depression, vertigo, obstructive cerebral blood vessel malady, spam, headache, pains, tolerance and dependence to morphine or azepin drugs, Alzheimer's disease, Parkinson's disease, osteoarthritis, viral arthritis, asthma, rheumatic arthritis, chronic arthritis, atopic dermatitis and the like. Particularly, a novel pyrimidine derivative (1) is excellent for curing asthma and atopic dermatitis.

The pyrimidine derivatives (1) of the present invention involving various derivatives as shown below.

(1) A pyrimidine derivative or pharmaceutically acceptable salt thereof, wherein $R^1$, $R^2$, $R^3$, $R^4$, $R^8$ and n are the same as defined in the above-mentioned general formula (1); and A is an oxygen atom.

(2) A pyrimidine derivative or pharmaceutically acceptable salt thereof, wherein $R^1$, $R^2$, $R^3$, $R^4$, $R^8$ and n are the same as defined in the above-mentioned general formula (1); and A is a sulfur atom.

(3) A pyrimidine derivative or pharmaceutically acceptable salt thereof, wherein $R^1$, $R^2$, $R^3$, $R^4$, $R^8$ and A are the same as defined in the above-mentioned general formula (1); and n is 1 to 2.

(4) A pyrimidine derivative or pharmaceutically acceptable salt thereof, wherein $R^1$, $R^2$, $R^3$, $R^4$, $R^8$ and A are the same as defined in the above-mentioned general formula (1); and n is 0.

(5) A pyrimidine derivative or pharmaceutically accept able salt thereof, wherein $R^1$, $R^2$, $R^3$, $R^4$ and $R^8$ are same as defined in the above-mentioned general formula (1); A is an oxygen atom; and n is 1 to 2.

(6) A pyrimidine derivative or pharmaceutically acceptable salt thereof, wherein $R^1$, $R^2$, $R^3$, $R^4$ and $R^8$ are the same as defined in the above-mentioned general formula (1); A is an oxygen atom; and n is 0.

(7) A pyrimidine derivative or pharmaceutically acceptable salt thereof, wherein $R^1$, $R^2$, $R^3$, $R^4$ and $R^8$ are the same as defined in the above-mentioned general formula (1); A is a sulfur atom; and n is 1 to 2.

(8) A pyrimidine derivative or pharmaceutically accept able salt thereof, wherein $R^1$, $R^2$, $R^3$, $R^4$ and $R^8$ are the same as defined in the above-mentioned general formula (1); A is a sulfur atom; and n is 0.

(9) A pyrimidine derivative or pharmaceutically accept able salt thereof, wherein $R^1$, $R^2$, $R^4$, $R^8$, A and n are the same as defined in the above-mentioned general formula (1); $R^3$ is a hydrogen atom, an alkyl group, a lower alkanoyl group, a phenyl group which may have the substituent(s) selected from the group consisting of a lower alkoxy group, a carboxyl group, a halogen-substituted-lower alkyl group and a lower alkyl group, or a lower alkoxy-lower alkyl group.

(10) A pyrimidine derivative or pharmaceutically acceptable salt thereof, wherein $R^1$, $R^2$, $R^4$, $R^8$, A and n are the same as defined in the above-mentioned general formula (1); and $R^3$ is an aralkyl group, a heterocyclic group, a cycloalkyl group, or a hydroxy-lower alkyl group.

(11) A pyrimidine derivative or pharmaceutically acceptable salt thereof, wherein $R^1$, $R^2$, $R^4$, $R^8$, A and n are the same as defined in the above-mentioned general formula (1); and $R^3$ is an alkyl group or a lower alkoxy-lower alkyl group.

(12) A pyrimidine derivative or pharmaceutically acceptable salt thereof, wherein $R^1$, $R^2$, $R^4$, $R^8$, A and n are the same as defined in the above-mentioned general formula (1); and $R^3$ is an alkyl group.

(13) A pyrimidine derivative or pharmaceutically acceptable salt thereof, wherein $R^1$, $R^2$, $R^4$, $R^8$, A and n are the same as defined in the above-mentioned general formula (1); and $R^3$ is a lower alkoxy-lower alkyl group.

(14) A pyrimidine derivative or pharmaceutically acceptable salt thereof, wherein $R^1$, $R^2$, $R^4$, $R^8$, A and n are the same as defined in the above-mentioned general formula (1); and $R^3$ is a lower alkyl group or a lower alkoxy-lower alkyl group.

(15) A pyrimidine derivative or pharmaceutically acceptable salt thereof, wherein $R^1$, $R^2$, $R^4$, $R^8$, A and n are the same as defined in the above-mentioned general formula (1); and $R^3$ is a lower alkyl group.

(16) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(17) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is an aralkyl group, a heterocyclic group, a cycloalkyl group, or a hydroxy-lower alkyl group.

(18) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is an alkyl group or a lower alkoxy-lower alkyl group.

(19) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is an alkyl group.

(20) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is a lower alkoxy-lower alkyl group.

(21) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is a lower alkyl group or a lower alkoxy-lower alkyl group.

(22) A pyrimidine derivative or pharmaceutically acceptable salt thereof, wherein $R^1$, $R^2$, $R^4$, $R^8$ and n are the same as defined in the above-mentioned general formula (1); A is an oxygen atom; and $R^3$ is a lower alkyl group.

(23) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(24) A pyrimidine derivative or pharmaceutically acceptable salts thereof, wherein $R^1$, $R^2$, $R^4$, $R^8$ and n are the same as defined in the above-mentioned general formula (1); A is a sulfur atom; and $R^3$ is an aralkyl group, a heterocyclic group, a cycloalkyl group, or a hydroxy-lower alkyl group.

(25) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is an alkyl group or a lower alkoxy-lower alkyl group.

(26) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is an alkyl group.

(27) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is a lower alkoxy-lower alkyl group.

(28) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is a lower alkyl group or a lower alkoxy-lower alkyl group.

(29) A pyrimidine derivative or pharmaceutically acceptable salt thereof, wherein $R^1$, $R^2$, $R^4$, $R^8$ and n are the same as defined in the above-mentioned general formula (1); A is a sulfur atom; and $R^3$ is a lower alkyl group.

(30) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(31) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is an aralkyl group, a heterocyclic group, a cycloalkyl group, or a hydroxy-lower alkyl group.

(32) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is an alkyl group or a lower alkoxy-lower alkyl group.

(33) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is an alkyl group.

(34) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is a lower alkoxy-lower alkyl group.

(35) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is a lower alkyl group or a lower alkoxy-lower alkyl group.

(36) A pyrimidine derivative or pharmaceutically acceptable salt thereof, wherein $R^1$, $R^2$, $R^4$ and $R^8$ are the same as defined in the above-mentioned general formula (1); n is 0; A is an oxygen atom; and $R^3$ is a lower alkyl group.

(37) A pyrimidine derivatives or pharmaceutically acceptable salt thereof, wherein $R^1$, $R^2$, $R^4$ and $R^8$ are the same as defined in the above-mentioned general formula (1); n is 0; A is a sulfur atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(38) A pyrimidine derivative or pharmaceutically acceptable salt thereof, wherein $R^1$, $R^2$, $R^4$ and $R^8$ are the same as defined in the above-mentioned general formula (1); n is 0; A is a sulfur atom; and $R^3$ is an aralkyl group, a heterocyclic group, a cycloalkyl group, or a hydroxy-lower alkyl group.

(39) A pyrimidine derivative or pharmaceutically acceptable salt thereof, wherein $R^1$, $R^2$, $R^4$ and $R^8$ are the same as defined in the above-mentioned general formula (1); n is 0; A is a sulfur atom; and $R^3$ is an alkyl group or a lower alkoxy-lower alkyl group.

(40) A pyrimidine derivative or pharmaceutically acceptable salt thereof, wherein $R^1$, $R^2$, $R^4$, and $R^8$ are the same as defined in the above-mentioned general formula (1); n is 0; A is a sulfur atom; and $R^3$ is an alkyl group.

(41) A pyrimidine derivative or pharmaceutically acceptable salt thereof, wherein $R^1$, $R^2$, $R^4$ and $R^8$ are the same as defined in the above-mentioned general formula (1); n is 0; A is a sulfur atom; and $R^3$ is a lower alkoxy-lower alkyl group.

(42) A pyrimidine derivative or pharmaceutically acceptable salt thereof, wherein $R^1$, $R^2$, $R^4$ and $R^8$ are the same as defined in the above-mentioned general formula (1); n is 0; A is a sulfur atom; and $R^3$ is a lower alkyl group or a lower alkoxy-lower alkyl group.

(43) A pyrimidine derivative or pharmaceutically acceptable salt thereof, wherein $R^1$, $R^2$, $R^4$ and $R^8$ are the same as defined in the above-mentioned general formula (1); n is 0; A is a sulfur atom; and $R^3$ is a lower alkyl group.

(44) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(45) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is an aralkyl group, a heterocyclic group, a cycloalkyl group, or a hydroxy-lower alkyl group.

(46) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is an alkyl group or a lower alkoxy-lower alkyl group.

(47) A pyrimidine derivatives or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is an alkyl group.

(48) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is a lower alkoxy-lower alkyl group.

(49) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is a lower alkyl group or a lower alkoxy-lower alkyl group.

(50) A pyrimidine derivative or pharmaceutically acceptable salt thereof, wherein $R^1$, $R^2$, $R^4$ and $R^8$ are the same as defined in the above-mentioned general formula (1); n is 1 to 2; A is an oxygen atom; and $R^3$ is a lower alkyl group.

(51) A pyrimidine derivative or pharmaceutically accept able salt thereof, wherein $R^1$, $R^2$, $R^4$ and $R^8$ are the same as defined in the above-mentioned general formula (1); n is 1 to 2; A is a sulfur atom; and $R^3$ is a hydrogen atom, an alkyl group, a lower alkanoyl group, a phenyl group which may have the substituent(s) selected from the group consisting of a lower alkoxy group, a carboxyl group, a halogen substituted-lower alkyl group and a lower alkyl group, or a lower alkoxy-lower alkyl group.

(52) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is an aralkyl group, a heterocyclic group, a cycloalkyl group or a hydroxy-lower alkyl group.

(53) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is an alkyl group or a lower alkoxy-lower alkyl group.

(54) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is an alkyl group.

(55) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is a lower alkoxy-lower alkyl group.

(56) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is a lower alkyl group or a lower alkoxy-lower alkyl group.

(57) A pyrimidine derivative or pharmaceutically acceptable salt thereof, wherein $R^1$, $R^2$, $R^4$ and $R^8$ are the same as defined in the above-mentioned general formula (1); n is 1 to 2; A is a sulfur atom; and $R^3$ is a lower alkyl group.

(58) A pyrimidine derivative or pharmaceutically acceptable salt thereof, wherein $R^1$, $R^4$, $R^8$, A and n are the same as defined in the above-mentioned general formula (1); $R^2$ and $R^3$ are combined to each other to form a 5- or 6-membered heterocyclic group.

(59) A pyrimidine derivative or pharmaceutically acceptable salt thereof, wherein $R^1$, $R^4$, $R^8$ and n are the same as defined in the above-mentioned general formula (1); A is an oxygen atom; $R^2$ and $R^3$ are combined to each other to form a 5- or 6-membered heterocyclic group.

(60) A pyrimidine derivative or pharmaceutically acceptable salt thereof, wherein $R^1$, $R^4$ and $R^8$ are the same as defined in the above-mentioned general formula (1); n is 0; A is an oxygen atom; $R^2$ and $R^3$ are combined to each other to form a 5- or 6-membered heterocyclic group.

(61) A pyrimidine derivative or pharmaceutically acceptable salt thereof, wherein $R^1$, $R^4$ and $R^8$ are the same as defined in the above-mentioned general formula (1); n is 1 to 2; A is an oxygen atom; $R^2$ and $R^3$ are combined to each other to form a 5- or 6-membered heterocyclic group.

(62) A pyrimidine derivative or pharmaceutically acceptable salt thereof, wherein $R^1$, $R^2$, $R^4$, $R^8$, A and n are the same as defined in the above-mentioned general formula (1); $R^3$ is an aralkyl group, a pyridyl group, a cycloalkyl group or a hydroxy-lower alkyl group.

(63) A pyrimidine derivative or pharmaceutically acceptable salt thereof, wherein $R^1$, $R^2$, $R^4$, $R^8$, A and n are the same as defined in the above-mentioned general formula (1); $R^3$ is a phenyl-lower alkyl group, a pyridyl group, a cycloalkyl group or a hydroxy-lower alkyl group.

Examples of each one of the substituents shown in the above-mentioned general formula (1) are specifically explained as follows.

As to the lower alkyl group, an alkyl group having 1 to 6 carbon atoms, such as methyl, ethyl, butyl, propyl, isopropyl, butyl, t-butyl, pentyl and hexyl groups can be exemplified.

As to the alkyl group as defined in R3, in addition to the above-mentioned alkyl groups, an alkyl group having 1 to 16 carbon atoms, such as heptyl, octyl, nonyl, decyl, undecyl and dodecyl groups can be exemplified.

As to the lower alkoxy group, an alkoxy group having 1 to 6 carbon atoms, such as methoxy, ethoxy, propoxy, isopropoxy, butoxy, t-butoxy, pentyloxy and hexyloxy groups can be exemplified.

As to the aralkyl group, an aralkyl group having 1 to 6 carbon atoms, such as benzyl, 1-phenylethyl, 2-phenylethyl, 3-phenylpropyl, 4-phenylbutyl, 5-phenylpentyl, 6-phenylhexyl, 1,1-dimethyl-2-phenylethyl and 2-methyl-2-phenylpropyl can be exemplified.

As to the cycloalkyl group, a cycloalkyl group having 3 to 8 carbon atoms, such as cyclopropyl, cyclopentyl, cyclohexyl, cycloheptyl and cyclooctyl groups can be exemplified.

As to the lower alkanoyl group, a straight chain- or branched chain-alkanoyl group having 1 to 6 carbon atoms, such as acetyl, propionyl, butyryl, isobutyryl, pentanoyl, t-butylcarbonyl and hexanoyl groups can be exemplified.

As to the hydroxy-lower alkyl group, a hydroxy-lower alkyl group having 1 to 6 carbon atoms, such as hydroxymethyl, 2-hydroxyethyl, 1,1-dimethyl-2-hydroxyethyl, 3-hydroxypropyl, 4-hydroxybutyl, 2-hydroxybutyl, 5-hydroxypentyl, 1-hydroxypentyl and 6-hydroxyhexyl groups can be exemplified.

As to the phenyl group which may have as the substituent selected from the group consisting of a hydrogen atom, a carboxyl group, a halogen substituted-lower alkyl group, a lower alkyl group and a lower alkoxy group, a phenyl group which may have as the substituent selected from the group consisting of a hydrogen atom, an alkyl group having 1 to 6 carbon atoms, an alkyl group having 1 to 6 carbon atoms with which halogen atoms are substituted, an alkoxy group having 1 to 6 carbon atoms and carboxyl group, such as phenyl, carboxyphenyl, tolyl, ethylpheyl, propylphenyl, butylphenyl, hexylphenyl, methoxyphenyl, ethoxyphenyl, butoxyphenyl, hexyloxyphenyl, monochloromethylphenyl, monobromomethylphenyl, monofluoromethylphenyl, dichloromethylphenyl, dibromomethylphenyl, difluoromethylphenyl, trichloromethylphenyl, tribromomethylphenyl, triiodomethylphenyl, trifluoromethylphenyl, 4-(1,2-dichloroethyl)phenyl, 2-(3-bromopropyl)phenyl, 3-(2,3,4-trifluorobutyl)phenyl and 4-(5-iodohexyl)phenyl groups can be exemplified.

As to the lower alkoxy-lower alkyl group, a lower alkoxy-lower alkyl group in which each one of the alkoxy moiety and alkyl moiety respectively having 1 to 6 carbon atoms, such as methoxymethyl, methoxyethyl, methoxybutyl, methyoxyhexyl, ethoxymethyl, propoxyethyl, isopropoxymethyl, methoxypropyl, butoxyethyl, t-butoxyhexyl, pentyloxyethyl, hexyloxymethyl and hexyloxypropyl groups can be exemplified.

Compounds represented by the general formula (1) of the present invention can be prepared by various methods, for example, they can be prepared by the following Reaction process step-1 to -10.

Reaction process step-1

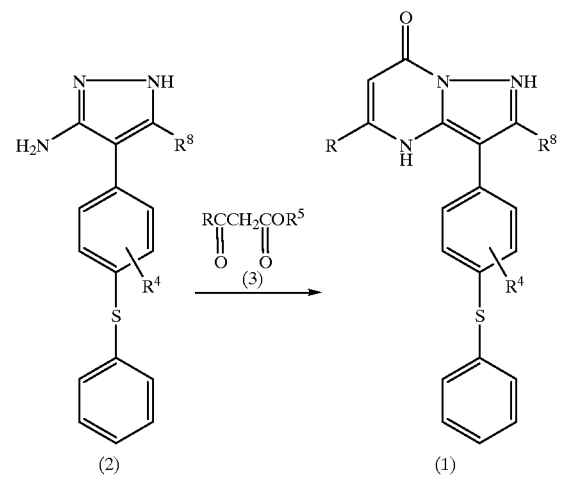

(wherein R, $R^4$ and $R^8$ are the same as defined previously; $R^5$ is a lower alkyl group or a phenylalkyl group which may have 1 to 3 substituents selected from the group consisting of nitro group, an alkoxy group and an alkyl group).

This reaction is carried out by reacting a compound represented by the general formula (2) with a compound represented by the general formula (3) in the absence or presence of a suitable solvent, in the presence of an acid, to obtain a compound represented by the general formula (1) of the present invention.

Examples of the above-mentioned solvent are halogenated hydrocarbons such as chloroform, dichloromethane and the like; aromatic hydrocarbons such as benzene, toluene and the like; and aprotic polar solvents such as N,N-dimethylformamide (DMF), dimethylsulfoxide (DMSO), acetonitrile and the like.

Examples of the above-mentioned acid are Lewis acids such as anhydrous aluminum chloride, stannic chloride, titanium tetrachloride, boron trichloride, complex of boron trifluoride-ethyl ether, zinc chloride and the like; inorganic acids such as phosphoric acid, hydrochloric acid, nitric acid, sulfuric acid and the like; and organic acids such as trichloroacetic acid, trifluoroacetic acid, methanesulfonic acid, acetic acid and the like.

Used ratio of a compound (3) to a compound (2) may be at least an equimolar quantity, preferably 1 to 2 times of the molar quantity. Used ratio of the acid to a compound (2) may be 1 to 50 times of the molar quantity, preferably 1 to 10 times of the molar quantity. The reaction is carried out at room temperature to 200° C., preferably at 100 to 110° C. and is finished in about 1 to 30 hours.

In case of that the terminal group of R is a hydroxyl group, then the reaction may be preferably carried out by protecting the hydroxyl group. After finished Reaction process step-1, said protecting group may be removed by methods in accordance with Reaction process step-2 and -3 as follows.

Reaction process step-2

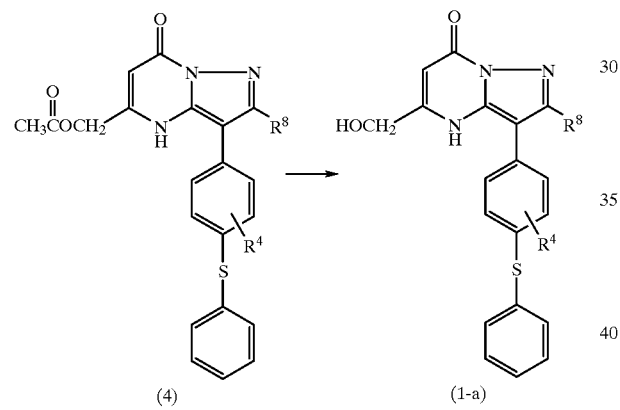

(wherein $R^4$ and $R^8$ are the same as defined previously).

This reaction is carried out by hydrolyzing a compound (4) obtained by Reaction process step-1 to obtain a compound represented by the general formula (1-a) of the present invention.

The reaction is carried out in a suitable solvent, and in the presence of a basic compound or acidic compound. Example of the solvent are alcohols such as methanol, ethanol and the like; and ethers such as dimethyl ether, diethyl ether, tetrahydrofuran, dioxane and the like.

Examples of the basic compound are, trialkylamines such as triethylamine, tributylamine and the like; organic basic compounds such as pyridine, picoline, 1,5-diazabicyclo[4.3.0]nonene-5, 1,4-diazabicyclo[2.2.2]-octane, 1,8-diazabicyclo[5.4.0]undecene-7 and the like; inorganic basic compounds for example, alkali metal hydroxides such as sodium hydroxide, potassium hydroxide and the like; alkali metal carbonates such as sodium carbonate, potassium carbonate and the like; and alkali metal hydrogencarbonates such as sodium hydrogencarbonate, potassium hydrogencarbonate and the like.

Examples of the acidic compound are Lewis acids such as anhydrous aluminum chloride, stannic chloride, titanium tetrachloride, boron trichloride and the like; inorganic acids such as hydrochloric acid, hydrobromic acid, nitric acid, sulfuric acid and the like; organic acids such as trichloroacetic acid, trifluoroacetic acid, methanesulfonic acid, acetic acid, formic acid and the like; further acidic type ion-exchange resins can be exemplified.

These basic compound or acidic compound may be used suitably in the ratio of 1 to 20 times the molar quantity, preferably 1 to 10 times the molar quantity to a compound (4). The reaction may be carried out at 0 to 150° C., preferably at 0° C. to room temperature, for about 1 to 24 hours.

Reaction process step-3

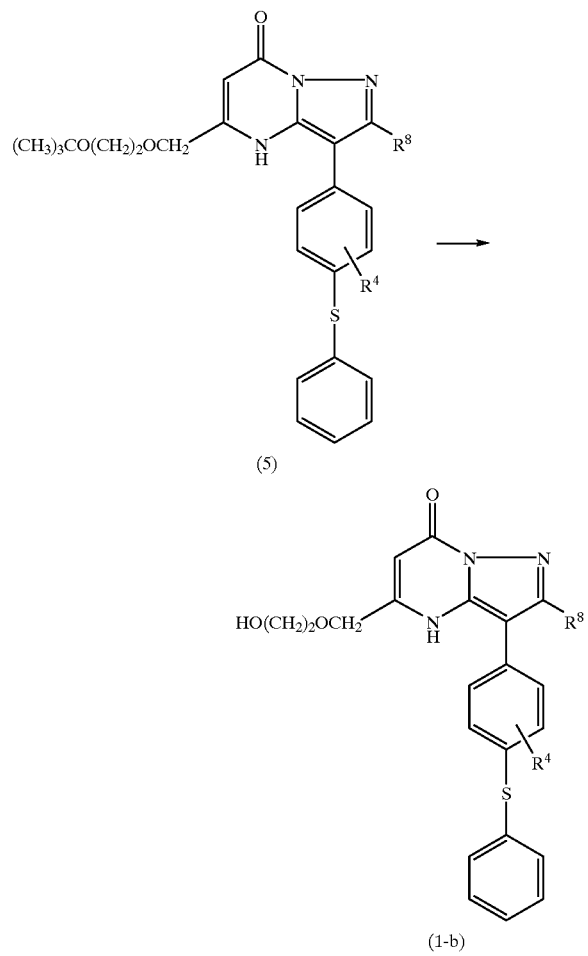

(wherein $R^4$ and $R^8$ are the same as defined previously).

This reaction gives a compound represented by the general formula (1-b) of the present invention by removing t-butyl group, which is a protecting group for the hydroxyl group, through hydrolysis.

This reaction is carried out in a suitable inert solvent, in the presence of an acidic compound. Examples of the inert solvent are alcohols such as methanol, ethanol and the like; halogenated hydrocarbons such as dichloromethane, dichloroethane, chloroform and the like.

As to the acid, for example Lewis acids such as anhydrous aluminum chloride, stannic chloride, titanium tetrachloride, boron trichloride and the like; inorganic acids such as hydrochloric acid, hydrobromic acid, nitric acid, sulfuric acid and the like; organic acids such as trichloroacetic acid, trifluoroacetic acid, methanesulfonic acid, acetic acid, formic acid and the like; further acidic type ion-exchange resins can be mentioned.

The acidic compound is used suitably in a ratio of 1 to 20 times the molar quantity, preferably 1 to 10 times the molar quantity to a compound (5). The reaction may be carried out at 0° C. to 100° C., preferably at 0° C. to room temperature, for about 1 to 30 hours.

Reaction process step-4

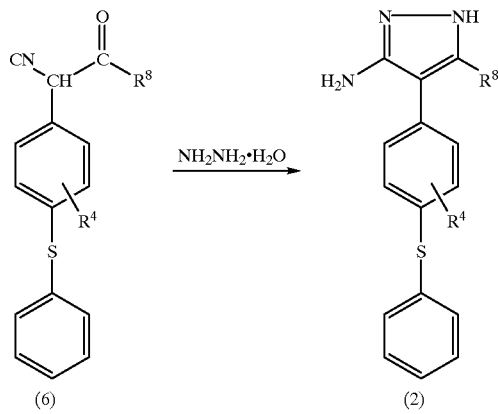

(wherein $R^4$ and $R^8$ are the same as defined previously).

This reaction gives a compound (2) by reacting a compound (6) with hydrazine ($NH_2NH_2.H_2O$) or its dihydrochloride or its sulfate in the presence of acetic acid or a mineral acid. The above-mentioned hydrazine may be used preferably in an amount of 1 to 2 times the molar quantity, and the reaction may be carried out preferably at room temperature to 100° C. Acetic acid or a mineral acid may be used preferably in an amount of 1 to 2 times the molar quantity to the hydrazine.

Reaction process step-5

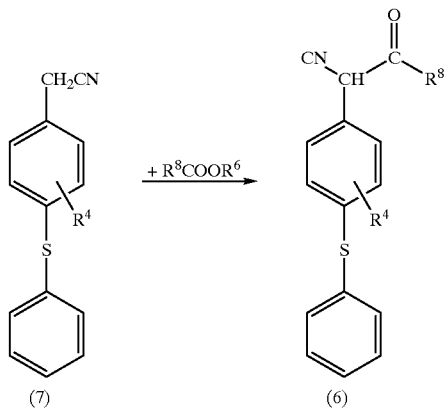

(wherein R and $R^8$ are the same as defined previously; $R^6$ is a lower alkyl group).

This reaction gives a compound (6) by reacting an acetonitrile derivative represented by the general formula (7) with a specific ester.

When a formic acid ester is used as the above-mentioned specific ester, then $R^8$ is a hydrogen atom. As to the formic acid ester, methyl formate, ethyl formate and the like may be exemplified.

This reaction is carried out in an inert solvent. Examples of the inert solvent are aromatic hydrocarbons such as benzene, toluene, xylene and the like; ethers such as diethyl ether, tetrahydrohydrofuran, dioxane and the like; N,N-dimethylformamide, dimethyl sulfoxide and the like. Used ratio of the ester to a compound (7) may be at least an equimolar quantity, preferably 1.05 to 1.25 times the molar quantity. Generally, the reaction may be carried out preferably under an ice-cooling condition for about 5 to 20 minutes, next at room temperature for about 4 to 15 hours. In order to proceed the reaction sufficiently, the reaction may be carried out preferably in the presence of at least an equimolar quantity of a sodium alkoxide such as sodium methoxide, or a metal hydride such as sodium hydride to the ester.

The reaction product (6) is obtained by adding water to the reaction mixture and separating the aqueous layer, then the pH of the aqueous layer is controlled to pH 3 to 4 by adding a mineral acid such as hydrochloric acid and to sediment the reaction product (6).

Reaction process step-6

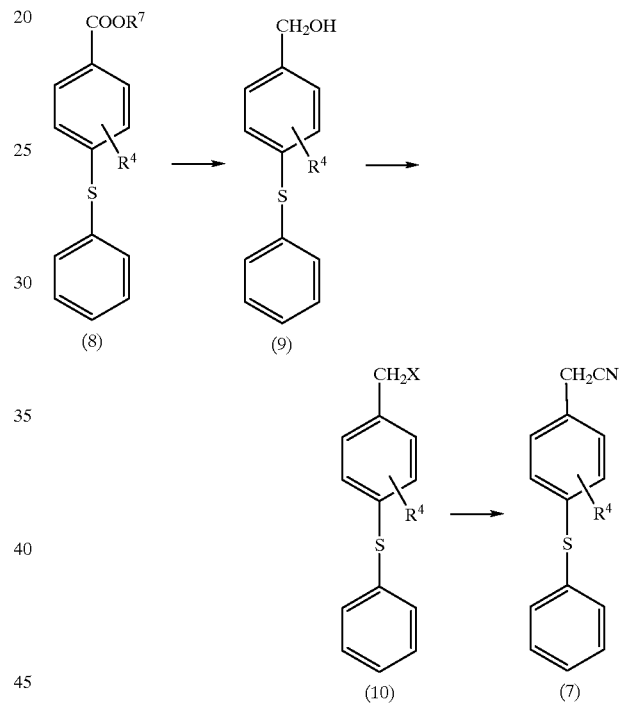

(wherein X is a halogen atom; $R^7$ is a lower alkyl group; and $R^4$ is the same as defined previously).

This Reaction process step-6 gives a compound of the general formula (9) by reducing a compound of the general formula (8) by use of a hydrogenation reducing agent, next this compound (9) is reacted with a halogenating agent to obtain a compound of the general formula (10), further, this compound of the general formula (10) is reacted with a cyanide compound to obtain a compound of the general formula (7) which is the starting material of Reaction process step-3.

The reaction for obtaining a compound (9) from a compound (8) is carried out in a suitable solvent. Examples of the solvent are ethers such as diethyl ether, tetrahydrofuran, dioxane, diglyme and the like; aliphatic hydrocarbons such as hexane, heptane and the like; aromatic hydrocarbons such as benzene, toluene and the like can be mentioned. Further, as to the hydrogenation reducing agent to be used in this reaction, lithium aluminum hydride, aluminum hydride, diisopropyl aluminum hydride, lithium borohydride, sodium borohydride-aluminum chloride, diborane and the like can be exemplified. Used amount of the hydrogenation reducing agent is at least 0.5 time the molar quantity, preferably about 0.6 to 1.2 times the molar quantity to a compound (8). The reaction is generally carried out under an ice-cooling condition to 100° C., preferably at 0 to 50° C., and is finished in about 30 minutes to 10 hours.

The reaction for obtaining a compound (10) from a compound (9) is carried out in the absence or presence of a suitable solvent. Examples of the solvent to be used in this reaction are ethers such as diethyl ether, tetrahydrofuran, dioxane and the like; halogenated hydrocarbons such as methylene chloride, chloroform, dichloroethane and the like; aromatic hydrocarbons such as benzene, toluene and the like. Further, examples of the halogenating agent to be used in this reaction are thionyl halides such as thionyl chloride, thionyl bromide and the like; hydrogen halides such as hydrogen chloride, hydrogen bromide, hydrogen iodide and the like; phosphorus halides such as phosphorus trichloride, phosphorus tribromide and the like. Used amount of the halogenating agent to a compound (9) may be at least an equimolar quantity, preferably 1 to 1.3 times the molar quantity. The reaction is carried out under an ice-cooling condition to at 100° C., preferably at about 0 to 50° C., and is finished in about 30 minutes to 5 hours.

The reaction for obtaining a compound (7) from a compound (10) is carried out in a suitable solvent. Examples of the solvent to be used in this reaction are lower alcohols such as methanol, ethanol, propanol and the like; aprotic polar solvents such as acetone, N,N-dimethylformamide (DMF), dimethyl sulfoxide (DMSO), hexamethylphosphoric triamide (HMPA) and the like; and mixed solvents of water with these solvents. Further, examples of the cyanide compound to be used in this reaction are potassium cyanide, sodium cyanide, silver cyanide, copper cyanide, calcium cyanide and the like can be exemplified. Used amount of the cyanation agent to a compound (10) may be at least an equimolar quantity, preferably 1 to 1.3 times the molar quantity. The reaction is carried out at room temperature to 150° C., preferably at room temperature to 100° C., and is finished in about 1 to 24 hours.

Reaction process step-7

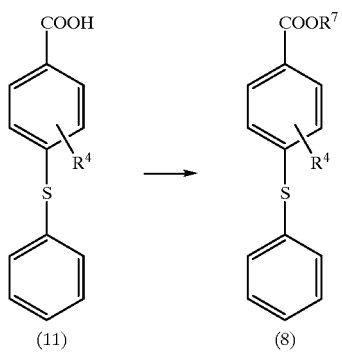

(11)   (8)

(wherein $R^4$ and $R^7$ are the same as defined previously). This reaction gives a compound represented by the general formula (8), which is the starting material of the above-mentioned Reaction process step-6, by subjecting a compound represented by the general formula (11) to a conventional esterification.

The above-mentioned esterification is carried out for example in the presence of a catalyst, by reacting a compound (11) with an alcohol represented by the formula:

$R^7$—OH (wherein $R^7$ is the same as defined previously).

As to the catalyst to be used in the esterification, a conventional catalyst for esterification can be used, concretely inorganic acids such as hydrogen chloride, concentrated sulfuric acid, phosphoric acid, a polyphosphoric acid, boron trifluoride, perchloric acid and the like; organic acids such as trifluoroacetic acid, trichloromethanesulfonic acid, naphthalenesulfonic acid, p-toluenesulfonic acid, benzenesulfonic acid, ethanesulfonic acid and the like; acid anhydrides such as trichloromethanesulfonic acid anhydride, trifluorometanesulfonic acid anhydride and the like; and catalysts such as thionyl chloride can be exemplified. Additionally, cation-exchange resins (acid type) can also be used. The above-mentioned esterification is carried out in the absence or presence of a suitable solvent. Examples of the solvent to be used are any conventional solvent being used for an esterification can be used, for example aromatic hydrocarbons such as benzene, toluene, xylene and the like; halogenated hydrocarbons such as dichloromethane, dichloroethane, chloroform and the like; ethers such as diethyl ether, tetrahydrofuran, dioxane and the like can be mentioned. Used ratio of the acid to a compound (11) may be an equimolar quantity to 100 times the molar quantity, preferably 10 to 30 times the molar quantity. The reaction may be carried out at −20° C. to 200° C., preferably at 0 to 150° C.

Additionally, a compound (8) can be obtained by a method for reacting an alkali metal salt (for example, sodium salt, potassium salt and the like) of a compound (11) with a halide compound represented by the general formula:

$R^7$—X (wherein $R^7$ and X are the same as defined previously); by a method of reacting a compound (11) with a diazoalkane such as diazomethane, diazoethane, diazopropane or the like; or by a method for reacting a compound (11) with an alcohol represented by the general formula:

$R^7$—OH (wherein $R^7$ is the same as defined previously) after conversion of the carboxy group of compound (11) into a reactive group (for example, acid chloride, amide or acid anhydride). These esterification can be carried out in accordance with a conventional method.

Reaction process step-8

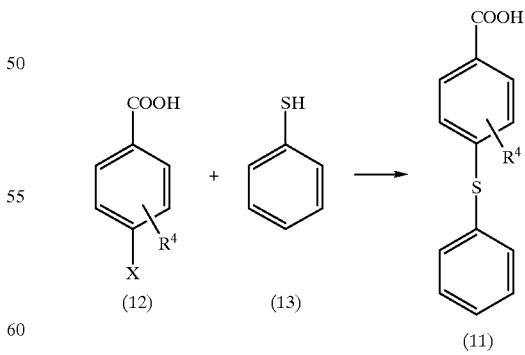

(12)   (13)   (11)

(wherein X and $R^4$ are the same as defined previously).

This reaction gives a compound represented by the general formula (11), which is the starting material of the above-mentioned Reaction process step-7, by reacting a benzoic acid derivative represented by the general formula

(12) with a phenylthio derivative represented by the general formula (13). The reaction is carried out in a suitable solvent in the presence of a basic compound such as sodium hydroxide, potassium hydroxide or the like. Examples of the solvent to be used are aprotic polar solvents such as N,N-dimethylformamide (DMF), N,N-dimethylacetamide, dimethyl sulfoxide (DMSO), hexamethylphosphoric triamide (HMPA) and the like.

Used ratio of a compound (13) to a compound (12) may be at least an equimolar quantity, preferably slightly excessive amount may be used. Further, in order to form a compound (11) and a salt of compound (12), at least 2 times the molar quantity, preferably a slightly excessive amount of the basic compound may be used to a compound (12). The reaction is generally carried out at room temperature to 180° C., and is finished in about 30 minutes to 24 hours.

Reaction process step-9

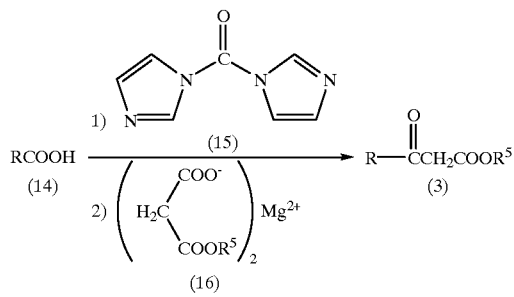

(wherein R and $R^5$ are the same as defined previously).

This reaction is a method for obtaining a compound (3) which is the starting material of Reaction process step-1.

A carboxylic acid represented by the general formula (14) is reacted with a condensing agent of 1,1'-carbonylbis-1H-imidazole (15), after the reaction, a compound (16) is added without separating the formed product and a compound (3) of the starting material of Reaction process step-1 is obtained.

As to the solvent to be used, inert solvents such as tetrahydrofuran (THF), N,N-dimethylformamide (DMF), dimethyl sulfoxide (DMSO), acetonitrile, toluene, 1,2-dimethoxyethane and the like can be exemplified.

Used ratio of 1,1'-carbonylbis-1H-imidazole and a compound (15) may be at least equimolar quantities, preferably 1 to 2 times the molar quantities to a compound (14).

The reaction is generally carried out at room temperature to 180° C., and is continued for 1 to 6 hours after addition of 1,1'-carbonylbis-1H-imidazole (15) to a compound (14), further adding a compound (16), the reaction is finished in about 1 to 30 hours.

Reaction process step-10

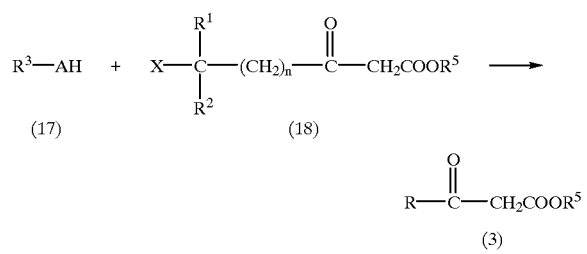

(wherein R, $R^1$, $R^2$, $R_3$, $R^5$, A and X are the same as defined previously).

This reaction is a different method for obtaining the starting material (3) of Reaction process step-1. Thus, after addition of sodium hydride to a compound (17), then thus obtained product is reacted with a compound (18) to obtain the starting material (3) of Reaction process step-1.

Examples of the solvent to be used in this reaction are, pyridine; halogenated hydrocarbons such as chloroform, dichloromethane and the like; aromatic hydrocarbons such as benzene, toluene and the like; aprotic polar solvents such as N,N-dimethylformamide (DMF), dimethyl sulfoxide (DMSO), acetonitrile and the like.

Used amount of sodium hydride to a compound (17) may be at least an equimolar quantity, preferably 1 to 5 times of the molar quantity. Further, used amount of a compound (18) to a compound (17) may be at least an equimolar quantity, preferably 1 to 2 times the molar quantity. Reaction is carried out at 0 to 150° C., and is finished in about 1 to 24 hours.

Pyrimidine derivatives represented by the general formula (1) of the present invention involve tautomers (1-A) and (1-B) as shown in the following equilibrium formula (i):

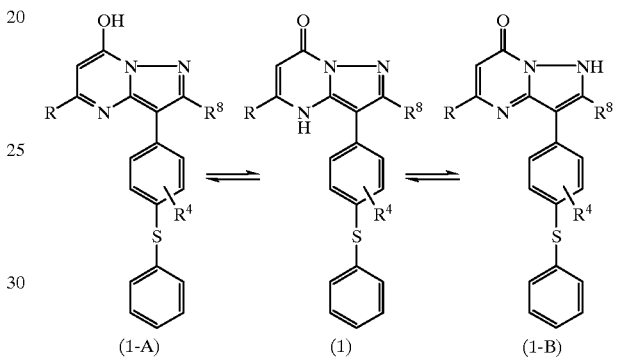

(wherein R, $R^4$ and $R^8$ are the same as defined previously).

Pyrimidine derivatives (1) of the present invention may contain optical isomers, syn-isomers and anti-isomers. These isomers can be separated by conventional separating methods, for example methods of optical resolution, methods by using enzymes and the like.

Pyrimidine derivative (1) of the present invention can be used generally in various forms of common pharmaceutical preparations. The pharmaceutical preparations are prepared by formulating with commonly employed diluents or excipients, such as fillers, extenders, binders, wetting agents, disintegrants, surfactants, lubricants and the like. The pharmaceutical preparations can be shaped into various forms and selected upon the curing purposes, thus typical examples of the forms are tablets, pills, powders, liquid medicines, supensions, emulsions, granules, capsules, suppositories, injection preparations (liquids, suspensions and the like), also they can be formulated as medicines for external use such as lotions, creams, ointments and the like.

In case of shaping the pharmaceutical preparations into the form of tablets, any known carriers which are used widely in this field can be applied. Examples of the carriers are, excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, calcium phosphate, polyvinylpyrrolidone and the like; disintegrators such as dry starch, sodium alginate, agar powder, laminarin powder, sodium hydrogencarbonate, calcium carbonate, polyoxyethylene sorbitan fatty acid esters, sodium lauryl sulfate, monoglyceride of stearic acid, starch, lactose and the like; disintegration inhibitors such as white sugar, stearin, cacao butter, hydrogenated oils and the like; absorption accelerators such as quaternary ammonium bases, sodium lauryl sulfate and the like; humectants such as glycerin, starch and the like; adsorbents such as starch, lactose, kaolin, bentonite, colloidal silicic acid and the like; and lubricants such as refined talc, stearic acid, boric acid powder, polyethylene glycols and the like can be mentioned. Further, in case of necessity, the tablets can be prepared in the form of common coated tablets, for example, sugar-coated tablets, gelatin film-coated tablets, enteric film coated tablets, film-coated tablets, or in the form of double-layer tablets, multiple-layers tablets and the like.

In case of shaping the pharmaceutical preparations into the form of pills, any known carriers which are used widely in this field can be applied. Examples of the carriers are, excipients such as glucose, lactose, starch, cacao butter, hydrogenated vegetable oils, kaolin, talc and the like; binders such as arabic gum powder, tragacanth gum powder, gelatin, ethanol and the like; and disintegrators such as laminarin, agaragar and the like.

In case of shaping the pharmaceutical preparations into the form of suppositories, any known carriers which are used widely in this field can be applied. Examples of the carriers are, polyethylene glycols, cacao butter, higher alcohols, esters of higher alcohols, gelatin, semi-synthesized glycerides and the like.

In case of shaping the pharmaceutical preparations into the form of injection preparations, solutions, emulsions and suspensions are sterilized and preferably they may be formulated as isotonic to the blood. In preparing the injection preparations as in the form of solutions, emulsions or suspensions, any known diluents which are used widely in this field can be applied. Examples of the diluents are water, ethanol, propylene glycol, ethoxylated isostearyl alcohol, polyoxylated isostearyl alcohol, fatty acid esters of polyoxyethylene sorbitan and the like. In case of prepare the injection preparations as isotonic to the blood, sufficient amount of sodium chloride, glucose or glycerin may be contained therein. Additionally, a dissolving additive, a buffer solution, an analgesic agent and the like which are commonly used may be contained therein. In case of necessity, a coloring agent, a preservatives, a purfume, a flavoring agent, a sweetening agent and other medicines may be contained therein.

In case of shaping the pharmaceutical preparations into external use preparations, for example as in the form of pastes, creams and gels, then diluents such as white petrolatum, paraffin, glycerin, cellulose derivatives, polyethylene glycols, silicones, bentonite and the like can be used.

The amount of pyrimidine derivative (1) or salt thereof of the present invention to be contained in pharmaceutical preparation is not particularly restricted and can be selected from a wide range, generally the amount may be selected within the range of 1 to 70% by weight in the whole composition of the preparation.

Method for administering pharmaceutical preparations according to the present invention is not particularly restricted, each one of these pharmaceutical preparation forms are administered according to the age of patient, the distinction of sex and other conditions, the degree of disease conditions and others. For example, tablets, pills liquids, suspensions, emulsions, granules and capsules are administered orally.

An injection preparation is intravenously administered singly or in combination with common auxiliary solutions such as glucose solution and amino acid solution. In case of necessity, it is singly administered intramuscularly, intradermally, subcutaneously or intraperitoneally.

A suppository is administered intrarectally. Further, an external preparation, such as lotion, cream, ointment and the like is coated on the diseased part.

Dosage of the above-mentioned pharmaceutical preparation is suitably selected depend upon the method of administration, the age of patient, the distinction of sex, and other conditions, as well as the degree of disease and other conditions, and generally the amount of pyrimidine derivative or salt thereof of the present invention may be in an amount of 1 to 100 mg, preferably 5 to 20 mg per 1 kg of the body weight per day, and such dosage can be administered dividedly in 2 to 4 times a day.

EXAMPLES

The present invention will be explained in detail by illustrating Reference examples and Examples as follows.

Reference Example 1

[Synthesis of 4-nitrobenzyl 4-ethoxyacetoacetate]

Under an ice-cooling condition, ethoxyacetic acid (0.95 ml) was added to a suspension of tetrahydrofuran (10 ml), containing 1,1'-carbonylbis-1H-imidazole (1.95 g), and the mixture was stirred at room temperature for 4 hours. Next, to this reaction mixture were added magnesium 4-nitrobenzyl malonate (6.01 g) and N,N-dimethylformamide (10 ml), and this mixture was stirred at room temperature. 18 Hours after the reaction, ethyl acetate was added to the reaction mixture, and the solid matters deposited were removed by filtration, then 10% hydrochloric acid was added to the thus obtained filtrate and the mixture was shaken. The organic layer separated from this mixture was washed with an aqueous solution saturated with sodium hydrogencarbonate, and an aqueous solution saturated with sodium chloride in this order, the washed organic layer was dried by adding anhydrous sodium sulfate thereto. After removal of the anhydrous sodium sulfate by filtration, the solvent was removed by distillation, there was obtained the above-mentioned desired compound (2.21 g).

$^1$H-NMR (CDCl$_3$) δ: 1.22 (t, J=7 Hz, 3H), 3.55 (q, J=7 Hz, 2H), 3.66 (s, 2H), 4.09 (s, 2H), 5.28 (s, 2H), 7.54 (d, J=8.9 Hz, 2H), 8.24 (d, J=8.9 Hz, 2H).

Reference Example 2

[Synthesis of 4-nitrobenzyl 4-t-butoxyacetoacetate]

Reactions were carried out similar to those of used in Reference example 1, except that the same molar quantity of t-butoxyacetic acid was used in place of ethoxyacetic acid, there was obtained the above-mentioned desired compound.

$^1$H-NMR (CDCl$_3$) δ: 1.20 (s, 9H), 3.68 (s, 2H), 4.00 (s, 2H), 5.27 (s, 2H), 7.54 (d, J=8.6 Hz, 2H), 8.23 (d, J=8.6 Hz, 2H).

Reference Example 3

[Synthesis of 4-nitrobenzyl β-oxo-tetrahydro-2-furanpropionate]

Reactions were carried out similar to those of used in Reference example 1, except that the same molar quantity of tetrahydro-2-francarboxylic acid was used in place of ethoxyacetic acid, there was obtained the above-mentioned desired compound.

$^1$H-NMR (CDCl$_3$) δ: 1.85–2.10 (m, 3H), 2.15–2.28 (m, 1H), 3.68–3.69 (m, 2H), 3.87–3.95 (m, 2H), 4.35–4.40 (m, 1H), 5.27 (s, 2H), 7.54 (d, J=8.8 Hz. 2H), 8.23 (d, J=8.8 Hz, 2H).

Reference Example 4

[Synthesis of 4-nitrobenzyl β-oxo-tetrahydro-2-pyranpropionate]

Reactions were carried out similar to those of used in Reference example 1, except that the same molar quantity of tetrahydro-2-pyranncarboxylic acid was used in place of ethoxyacetic acid, there was obtained the above-mentioned desired compound.

$^1$H-NMR (CDCl$_3$) δ: 1.40–1.59 (m, 4H), 1.90–2.16 (m, 2H), 3.39–3.49 (m, 1H), 3.66 (d, J=16.5 Hz, 1H), 3.74 (d, J=16.8 Hz, 1H), 3.85 (dd, J=2.3 Hz, 10.9 Hz, 1H), 4.01 (d, J=12.2 Hz. 1H), 5.27 (s, 2H), 7.54 (d, J=8.6 Hz, 2H), 8.23 (d, J=8.9 Hz, 2H).

Reference Example 5
[Synthesis of 4-nitrobenzyl 5-ethoxy-3-oxopentanate]

Reactions were carried out similar to those of used in Reference example 1, except that the same molar quantity of 3-ethoxypropionic acid was used in place of ethoxyacetic acid, there was obtained the above-mentioned desired compound.

$^1$H-NMR (CDCl$_3$) δ: 1.17 (t, J=7 Hz, 3H), 2.78 (t, J=6 Hz, 2H), 3.48 (q, J=7 Hz, 2H), 3.62 (s, 2H), 3.69 (t, J=6 Hz, 2H), 5.27 (s, 2H), 7.54 (d, J=9 Hz, 2H), 8.24 (d, J=9 Hz, 2H).

Reference Example 6
[Synthesis of 4-nitrobenzyl 5-methoxy-3-oxopentanate]

Reactions were carried out similar to those of used in Reference Example 1, except that the same molar quantity of 3-methoxypropionic acid was used in place of ethoxyacetic acid, there was obtained the above-mentioned desired compound.

$^1$H-NMR (CDCl$_3$) δ: 2.78 (t, J=6 Hz, 2H), 3.33 (s, 3H), 3.61 (s, 2H), 3.66 (t, J=6 Hz, 2H), 5.27 (s, 2H), 7.54 (d, J=8 Hz, 2H), 8.23 (d, J=8 Hz, 2H).

Reference Example 7
[Synthesis of 4-nitrobenzyl 6-methoxy-3-oxohexanate]

Reactions were carried out similar to those of used in Reference Example 1, except that the same molar quantity of 4-methoxybutyric acid was used in place of ethoxyacetic acid, there was obtained the above-mentioned desired compound.

$^1$H-NMR (CDCl$_3$) δ: 1.83–1.93 (m, 2H), 2.64 (t, J=7 Hz, 2H), 3.29 (s, 3H), 3.34–3.41 (m, 2H), 3.59 (s, 2H), 5.28 (s, 2H), 7.54 (d, J=8 Hz, 2H), 8.22 (d, J=8 Hz, 2H)

Reference Example 8
[Synthesis of 4-nitrobenzyl 4,4-dimethoxyacetoacetate]

Reactions were carried out similar to those of used in Reference Example 1, except that the same molar quantity of dimethoxyacetic acid was used in place of ethoxyacetic acid, there was obtained the above-mentioned desired compound.

$^1$H-NMR (CDCl$_3$) δ: 3.42 (s, 6H), 3.69 (s, 2H), 4.55 (s, 1H), 5.28 (s, 2H), 7.54 (d, J=9 Hz, 2H), 8.23 (d, J=9 Hz, 2H).

Reference Example 9
[Synthesis of 4-nitrobenzyl 4,4-diethoxyacetoacetate]

Reactions were carried out similar to those of used in Reference Example 1, except that the same molar quantity of diethoxyacetic acid was used in place of ethoxyacetic acid, there was obtained the above-mentioned desired compound.

$^1$H-NMR (CDCl$_3$) δ: 1.23 (t, J=7 Hz, 6H), 3.5–3.8 (m, 6H), 4.65, (s, 1H), 5.28 (s, 2H), 7.54 (d, J=8.9 Hz, 2H), 8.23 (d, J=8 Hz, 2H).

Reference Example 10
[Synthesis of 4-nitrobenzyl 5,5-dimethoxy-3-oxopentanate]

Reactions were carried out similar to those of used in Reference Example 1, except that the same molar quantity of 3,3-dimethoxypropionic acid was used in place of ethoxyacetic acid, there was obtained the above-mentioned desired compound.

$^1$H-NMR (CDCl$_3$) δ: 2.85 (d, J=5.3 Hz, 2H), 3.36 (s, 6H), 3.62 (s, 2H), 4.76 (t, J=5.3 Hz, 1H), 5.28 (s, 2H), 7.54 (d, J=8.6 Hz, 2H), 8.23 (d, J=8.6 Hz, 2H).

Reference Example 11
[Synthesis of 4-nitrobenzyl 5,5-ethylenedioxy-3-oxohexanate]

Reactions were carried out similar to those of used in Reference Example 1, except that the same molar quantity of 3,3-ethylenedioxybutyric acid was used in place of ethoxyacetic acid, there was obtained the above-mentioned desired compound.

$^1$H-NMR (CDCl$_3$) δ: 1.40 (s, 3H), 2.89 (s, 2H), 3.69 (s, 2H), 3.94–4.00 (m, 4H), 5.27 (s, 2H), 7.54 (d, J=8.3 Hz, 2H), 8.23 (d, J=8.6 Hz, 2H).

Reference Example 12
[Synthesis of 4-nitrobenzyl 6,6-ethylenedioxy-3-oxoheptanate]

Reactions were carried out similar to those of used in Reference Example 1, except that the same molar quantity of 4,4-ethylenedioxyvaleric acid was used in place of ethoxyacetic acid, there was obtained the above-mentioned desired compound.

$^1$H-NMR (CDCl$_3$) δ: 1.31 (s, 3H), 2.02 (t, J=7.3 Hz, 2H), 2.61 (t, J=7.3 Hz, 2H), 3.58 (s, 2H), 3.85–3.97 (m, 4H), 5.27 (s, 2H), 7.54 (d, J=8.6 Hz, 2H), 8.23 (d, J=8.6 Hz, 2H).

Reference Example 13
[Synthesis of 4-nitrobenzyl 4-methylthioacetoacetate]

Reactions were carried out similar to those of used in Reference Example 1, except that the same molar quantity of methylthioacetic acid was used in place of ethoxyacetic acid, there was obtained the above-mentioned desired compound.

$^1$H-NMR (CDCl$_3$) δ: 2.06(s, 3H), 3.30 (s, 2H) 3.79 (s, 2H), 5.28 (s, 2H), 7.54 (d, J=8.6 Hz, 2H), 8.23 (d, J=8.6 Hz, 2H).

Reference Example 14
[Synthesis of 4-nitrobenzyl 4-ethylthioacetoacetate]

Reactions were carried out similar to those of used in Reference Example 1, except that the same molar quantity of ethylthioacetic acid was used in place of ethoxyacetic acid, there was obtained the above-mentioned desired compound.

$^1$H-NMR (CDCl$_3$) δ: 1.23 (t, J=7.3 Hz, 3H), 2.49 (q, J=7.3 Hz, 2H), 3.34 (s, 2H), 3.80 (s, 2H), 5.28 (s, 2H), 7.54 (d, J=9 Hz, 2H), 8.23 (d, J=9 Hz, 2H).

Reference Example 15
[Synthesis of 4-nitrobenzyl 5-methylthio-3-oxopentanate]

Reactions were carried out similar to those of used in Reference Example 1, except that the same molar quantity of 3-methylthiopropionic acid was used in place of ethoxyacetic acid, there was obtained the above-mentioned desired compound.

$^1$H-NMR (CDCl$_3$) δ: 2.11 (s, 3H), 2.72–2.90 (m, 4H), 3.59 (s, 2H), 5.28 (s, 2H), 7.54 (d, J=8.2 Hz, 2H), 8.23 (d, J=8.6 Hz, 2H).

Reference Example 16
[Synthesis of 4-nitrobenzyl 3-oxo-5-(2-pyridylthio)pentanate]

Reactions were carried out similar to those of used in Reference Example 1, except that the same molar quantity of 3-(2-pyridylthio)propionic acid was used in place of ethoxyacetic acid, there was obtained the above-mentioned desired compound.

$^1$H-NMR (CDCl$_3$) δ: 3.04 (t, J=7 Hz, 2H), 3.39 (t, J=7 Hz, 2H), 3.58 (s, 2H), 5.26 (s, 2H), 6.98 (dd, J=5.0 Hz, 7.3 Hz, 1H), 7.14 (d, J=7.6 Hz, 1H), 7.44–7.54 (m, 3H), 8.21 (d, J=8.6 Hz, 2H), 8.39 (d, J=5.0 Hz, 1H).

Reference Example 17

[Synthesis of 4-nitrobenzyl 6-ethylthio-3-oxohexanate]

Reactions were carried out similar to those of used in Reference Example 1, except that the same molar quantity of 4-ethylthiobutyric acid was used in place of ethoxyacetic acid, there was obtained the above-mentioned desired compound.

$^1$H-NMR (CDCl$_3$) δ: 1.24 (t, J=7.3 Hz, 3H), 1.85–1.95 (m, 2H), 2.46–2.57 (m, 4H), 2.69 (t, J=7 Hz, 2H), 3.57 (s, 2H), 5.27 (s, 2H), 7.54 (d, J=8.2 Hz, 2H), 8.24 (d, J=8.6 Hz, 2H).

Reference Example 18

[Synthesis of ethyl 4-cyclopentyloxyacetoacetate]

Under nitrogen gas stream, into a suspension of 1,2-dimethoxyethane (20 ml) containing sodium hydride (1.3 g) was added cyclopentylalcohol (2.36 ml) under an ice-cooling condition and the mixture was stirred at room temperature. 15 Minutes after the stirring, ethyl 4-chloroacetoacetate (3.29 g) was added thereto under an ice-cooling condition and stirred at room temperature for 18 hours. Next, under an ice-cooling condition, the reaction mixture was neutralized with 10% hydrochloric acid, then extracted with diethyl ether. The organic layer was washed with an aqueous solution saturated with sodium chloride, an aqueous solution saturated with sodium hydrogencarbonate, and an aqueous solution saturated with sodium chloride in this order, then the washed organic layer was dried with anhydrous sodium sulfate, and the solvent was removed by distillation. The residue was purified by subjecting a silica gel column chromatography (silica gel: manufactured by Merck & Co., eluate:diethyl ether:n-hexane=1:4). there was obtained the above-mentioned desired compound (2.55 g).

$^1$H-NMR (CDCl$_3$) δ: 1.28 (t, J=7 Hz, 3H), 1.53–1.71 (m, 8H), 3.52 (s, 2H), 3.92–3.98 (m, 1H) 4.04 (s, 2H), 4.19 (q, J=7 Hz, 2H).

Reference Example 19

[Synthesis of ethyl 4-(3,7-dimethyloctyloxy)acetoacetate]

Reactions were carried out similar to those of used in Reference Example 18, except that the same molar quantity of 3,7-dimethyloctanol was used in place of cyclopentyl alcohol, there was obtained the above-mentioned desired compound.

$^1$H-NMR (CDCl$_3$) δ: 0.85–0.90 (m, 9H), 1,10–1.68 (m, 13H), 3.44–3.54 (m, 2H), 3.53 (s, 2H), 4.09 (s, 2H), 4.16–4.25 (m, 2H).

Reference Example 20

[Synthesis of ethyl 4-(tetrahydropyran-4-yloxy) acetoacetate]

Reactions were carried out similar to those of used in Reference Example 18, except that the same molar quantity of tetrahydropyran-4-ol was used in place of cyclopentyl alcohol, there was obtained the above-mentioned desired compound.

$^1$H-NMR (CDCl$_3$) δ: 1.29 (t, J=7.3 Hz, 3H), 1,56–1.69 (m, 2H), 1.89–1.93 (m, 2H), 3.41–3.50 (m, 3H), 3.55 (s, 2H), 3.90–3.98 (m, 2H), 4.15 (s, 2H), 4.20 (q, J=7.3 Hz, 2H).

Reference Example 21

[Synthesis of ethyl 4-(2-t-butoxyethoxy)acetoacetate]

Reactions were carried out similar to those of used in Reference Example 18, except that the same molar quantity of ethylene glycol mono-t-butyl ether was used in place of cyclopentyl alcohol, there was obtained the above-mentioned desired compound.

$^1$H-NMR (CDCl$_3$) δ: 1.20 (s, 9H), 1.28 (t, J=7 Hz, 3H), 3.52–3.56 (m, 2H), 3.57 (s, 2H), 3.62–3.66 (m, 2H), 4.20 (s, 2H), 4.20 (q, J=7 Hz, 2H).

Reference Example 22

[Synthesis of ethyl 4-(3-methoxypropoxy)acetoacetate]

Reactions were carried out similar to those of used in Reference Example 18, except that the same molar quantity of 3-methoxypropanol was used in place of cyclopentyl alcohol, there was obtained the above-mentioned desired compound.

$^1$H-NMR (CDCl$_3$) δ: 1.28 (t, J=7 Hz, 3H), 1.83–1.92 (m, 2H), 3.34 (s, 3H), 3.47 (t, J=6 Hz, 2H), 3.53 (s, 2H),3.58 (t, J=6 Hz, 2H), 4.11 (s, 2H), 4.20 (q, J=7 Hz, 2H).

Reference Example 23

[Synthesis of ethyl 4-(3-ethoxypropoxy)acetoacetate]

Reactions were carried out similar to those of used in Reference Example 18, except that the same molar quantity of 3-ethoxypropanol was used in place of cyclopentyl alcohol, there was obtained the above-mentioned desired compound.

$^1$H-NMR (CDCl$_3$) δ: 1.20 (t, J=7 Hz, 3H), 1.28 (t, J=7 Hz, 3H), 1.83–1.92 (m, 2H), 3.44–3.52 (m, 4H), 3.53 (s, 2H), 3.59 (t, J=6.3 Hz, 2H), 4.11 (s, 2H), 4.20 (q, J=7 Hz, 2H).

Reference Example 24

[Synthesis of ethyl 4-(2-pyridylthio)acetoacetate]

Reactions were carried out similar to those of used in Reference Example 18, except that the same molar quantity of 2-mercaptopyridine was used in place of cyclopentyl alcohol, there was obtained the above-mentioned desired compound.

$^1$H-NMR (CDCl$_3$) δ: 1.28 (t, J=7 Hz, 3H), 3.70 (s, 2H), 4.05 (s, 2H), 4.20 (q, J=7 Hz, 2H), 7.00 (dd, J=4.96 Hz, 7.26 Hz, 1H), 7.23 (d, J=7.9 Hz, 1H), 7.50 (m, 1H), 8.36 (d, J=4.3 Hz, 1H).

Reference Example 25

[Synthesis of ethyl 4-(3-methylphenoxy)acetoacetate]

Reactions were carried out similar to those of used in Reference Example 18, except that the same molar quantity of m-cresol was used in place of cyclopentyl alcohol, there was obtained the above-mentioned desired compound.

$^1$H-NMR (CDCl$_3$) δ: 1.26 (t, J=7 Hz, 3H), 2.33 (s, 3H), 3.63 (s, 2H), 4.19 (q, J=7 Hz, 2H), 4.62 (s, 2H), 5.39–6.74 (m, 2H), 6.82 (d, J=8 Hz, 1H), 7.18 (t, J=8 Hz, 1H).

Reference Example 26

[Synthesis of ethyl 4-(3-trifluoromethylphenoxy) acetoacetate]

Reactions were carried out similar to those of used in Reference Example 18, except that the same molar quantity of 3-trifluoromethylphenol was used in place of cyclopentyl alcohol, there was obtained the above-mentioned desired compound.

$^1$H-NMR (CDCl$_3$) δ: 1.26 (t, J=7 Hz, 3H), 3.64 (s, 2H), 4.20 (q, J=7 Hz, 2H), 4.72 (s, 2H), 7.06–7.14 (m, 2H), 7.26–7.29 (m, 1H), 7.43 (t, J=8 Hz, 1H).

Reference Example 27

[Synthesis of ethyl 4-(3-methoxyphenoxy)acetoacetate]

Reactions were carried out similar to those of used in Reference Example 18, except that the same molar quantity of 3-methoxyphenol was used in place of cyclopentyl alcohol, there was obtained the above-mentioned desired compound.

$^1$H-NMR (CDCl$_3$) δ: 1.30 (m, 3H), 3.63 (s, 2H), 3.79 (s, 3H), 4.20 (m, 2H), 4.63 (s, 2H), 6.40–6.60 (m 3H), 7.10–7.30 (m, 1H).

Reference Example 28
[Synthesis of ethyl 4-(4-carboxyphenoxy)acetoacetate]

Under nitrogen gas stream, into a suspension of dimethylformamide (5 ml) containing sodium hydride (0.72 g) was added a solution of dimethylformamide (5 ml) containing 4-hydroxybenzoic acid (0.69 g) under an ice-cooling condition and the mixture was stirred at room temperature. One hour after the stirring, ethyl 4-chloroacetoacetate (0.82 g) was added thereto under an ice-cooling condition and stirred at room temperature for 18 hours. Next, under an ice-cooling condition, the reaction mixture was acidified with 10% hydrochloric acid, then extracted with ethyl acetate. The organic layer was washed with an aqueous solution saturated with sodium chloride, then the washed organic layer was dried with anhydrous sodium sulfate, and the solvent was removed by distillation. The residue was purified by subjecting a silica gel column chromatography (silica gel: manufactured by Merck & Co., eluant:chloroform:methanol:acetic acid=98:2:1), there was obtained the above-mentioned desired compound (0.32 g).

$^1$H-NMR (CDCl$_3$) δ: 1.96 (t, J=7 Hz, 3H), 3.72 (s, 2H), 4.12 (q, J=7 Hz, 2H), 5.02 (s, 2H), 6.99 (d, J=8.3 Hz, 2H), 7.87 (d, J=8.3 Hz, 2H), 12.7 (brs, 1H).

Example 1
[Synthesis of 4,7-dihydro-5-methoxymethyl-7-oxo-3-(4-phenylthiophenyl)pyrazolo[1,5-a]pyrimidine]

A mixture of 3-amino-4-(4-phenylthiophenyl)pyrazole (0.27 g) which was prepared in accordance with the method disclosed in WO 92/06096, methyl 4-methoxyacetoacetate (0.14 ml) and acetic acid (0.5 ml) was heated at 100 to 110° C. and stirred. After 3 hours, ethyl alcohol was added to the reaction mixture and concentrated under a reduced pressure. To the residue thus obtained was added ethyl acetate and stirred under an ice-cooled condition. The deposited solid matters were as collected by filtration, and washed with ethyl acetate and then dried, there was obtained the above-mentioned desired compound (0.28 g).

Melting point: 163–165° C.; $^1$H-NMR (CDCl$_3$) δ: 3.52 (s, 3H), 4.53 (s, 2H), 5.77 (s, 1H), 7.28–7.39 (m, 9H), 7.95 (s, 1H), 9.66 (brs, 1H).

Example 2
[Synthesis of 4,7-dihydro-5-ethoxymethyl-7-oxo-3-(4-phenylthiophenyl)pyrazolo[1,5-a]pyrimidine]

Reactions were carried out similar to those of used in Example 1, except that the same molar quantity of 4-nitrobenzyl 4-ethoxyacetoacetate, obtained in Reference Example 1, was used in place of methyl 4-methoxyacetoacetate, there was obtained the above-mentioned desires compound.

Melting point: 169–171° C.; $^1$H-NMR (DMSO-d$_6$) δ: 1.18 (t, J=7 Hz, 3H), 3.56 (q, J=7 Hz, 2H), 4.46 (s, 2H), 5.82 (s, 1H), 7.32–7.42 (m, 7H), 7.57 (d, J=7.92 Hz, 2H), 8.17 (s, 1H), 12.0 (s, 1H).

Example 3
[Synthesis of 5-cyclopentyloxymethyl-4,7-dihydro-7-oxo-3-(4-phenylthiophenyl)pyrazolo[1,5-a]-pyrimidine]

Reactions were carried out similar to those of used in Example 1, except that the same molar quantity of methyl 4-cyclopentyloxyacetoacetate, obtained in Reference Example 18, was used in place of methyl 4-methoxyacetoacetate, there was obtained the above-mentioned desires compound.

Melting point: 207–210° C.; $^1$H-NMR (CDCl$_3$) δ: 1.58–1.81 (m, 8H), 4.09–4.13 (m, 1H), 4.53 (s, 2H), 5.75 (s, 1H), 7.26–7.39 (m, 9H), 7.99 (s, 1H), 9.43 (brs, 1H).

Example 4
[Synthesis of 5-cyclohexyloxymethyl-4,7-dihydro-7-oxo-3-(4-phenylthiophenyl)pyrazolo[1,5-a]-pyrimidine]

Reactions were carried out similar to those of used in Example 1, except that the same molar quantity of ethyl 4-cyclohexyloxyacetoacetate was used in place of methyl 4-methoxyacetoacetate, there was obtained the above-mentioned desired compound.

Melting point: 220–224° C.; $^1$H-NMR (CDCl$_3$) δ: 1.23–1.94 (m, 10H), 3.45–3.52 (m, 1H), 4.60 (s, 2H), 5.76 (s, 1H), 7.25–7.41 (m, 9H), 7.99 (s, 1H), 9.58 (brs, 1H).

Example 5
[Synthesis of 4,7-dihydro-5-isopropoxymethyl-7-oxo-3-(4-phenylthiophenyl)pyrazolo[1,5-a]pyrimidine]

A mixture of 3-amino-4-(4-phenylthiophenyl)pyrazole (0.3 g), ethyl 4-isopropoxyacetoacetate (0.4 g) and acetic acid (0.5 ml) was heated at 100 to 110° C. and stirred. 3 Hours after, the reaction mixture was diluted with ethyl acetate and the organic layer was washed with water and an aqueous solution saturated with sodium chloride in this order, then dried with anhydrous sodium sulfate. After removal of the solvent by distillation, the residue thus obtained was purified by a silica gel column chromatography (silica gel was the same as defined above; eluant:ethyl acetate:n-hexane=3:1), there was obtained the above-mentioned desired compound (0.25 g).

Melting point: 146–151° C.; $^1$H-NMR (CDCl$_3$) δ: 1.27 (d, J=6.3 Hz, 6H), 3.76–3.85 (m, 1H), 4.55 (s, 2H), 5.75 (s, 1H), 7.29–7.44 (m, 9H), 8.04 (s, 1H), 9.23 (brs, 1H).

Example 6
[Synthesis of 5-t-butoxymethyl-4,7-dihydro-7-oxo-3-(4-phenylthiophenyl)pyrazolo[1,5-a]pyrimidine]

Reactions were carried out similar to those of used in Example 5, except that the same molar quantity of 4-nitrobenzyl 4-t-butoxyacetoacetate, obtained in Reference Example 2, was used in place of ethyl 4-isopropoxyacetoacetate, there was obtained the above-mentioned desired compound.

Melting point: 113–116° C.; $^1$H-NMR (CDCl$_3$) δ: 1.29 (s, 9H), 4.52 (s, 2H), 5.80 (s, 1H), 7.28–7.36 (m, 9H), 7.98 (s, 1H).

Example 7
[Synthesis of 5-benzyloxymethyl-4,7-dihydro-7-oxo-3-(4-phenylthiophenyl)pyrazolo-[1,5-a]pyrimidine]

Reactions were carried out similar to those of used in Example 1, except that the same molar quantity of ethyl 4-benzyloxyacetoacetate was used in place of methyl 4-methoxyacetoacetate, there was obtained the above-mentioned desired compound.

Melting point: 183–186° C.; $^1$H-NMR (DMSO-d$_6$) δ: 4.53 (s, 2H), 4.63 (s, 2H), 5.88 (s, 1H), 7.30–7.43 (m, 12H), 7.56 (d, J=8.25 Hz, 2H), 8.16 (s, 1H), 12.0 (s, 1H).

Example 8
[Synthesis of 4,7-dihydro-5-(3,7-dimethyloctyloxymethyl)-7-oxo-3-(4-phenylthiophenyl)pyrazolo[1,5-a]pyrimidine]

Reactions were carried out similar to those of used in Example 5, except that the same molar quantity of ethyl 4-(3,7-dimethyloctyloxy)acetoacetate, obtained in Reference Example 19, was used in place of ethyl 4-isopropoxyacetoacetate, there was obtained the above-mentioned desired compound.

$^1$H-NMR (CDCl$_3$) δ: 0.86 (t, J=6.6 Hz, 9H), 1.10–1.63 (m, 10H), 3.63 (t, J=6.6 Hz, 2H), 4.52 (s, 2H), 5.78 (s, 1H), 7.28–7.40 (m, 9H), 8.03 (s, 1H).

Example 9

[Synthesis of 5-acetoxymethyl-4,7-dihydro-7-oxo-3-(4-phenylthiophenyl)pyrazolo[1,5-a]pyrimidine]

Reactions were carried out similar to those if used in Example 1, except that the same molar quantity of ethyl 4-acetoxyacetate was used in place of ethyl 4-methoxyacetoacetate, there was obtained the above-mentioned desired compound.

Melting point: 118–130° C.; $^1$H-NMR (DMSO-d$_6$) δ: 2.14 (s, 3H), 5.06 (s, 2H), 5.89 (s, 1H), 7.31–7.42 (m, 7H), 8.10 (br, 2H), 8.36 (brs, 1H), 12.1 (brs, 1H).

Example 10

[Synthesis of 4,7-dihydro-5-hydroxymethyl-7-oxo-3-(4-phenylthiophenyl)pyrazolo[1.5-a]pyrimidine]

Into a methanol suspension (15 ml) containing 5-acetoxymethyl-4,7-dihydro-7-oxo-3-(4-phenylthiophenyl)pyrazolo[1.5-a]pyrimidine (0.4 g), obtained in Example 9, was added an aqueous solution of 2N-sodium hydroxide (5 ml), and the mixture was stirred at room temperature. 4 Hours after, under an ice-cooling condition, pH of the reaction mixture was adjusted to pH 1–3 by adding 10% hydrochloric acid, then water was added and stirred for 1 hour. Then the deposit was collected by filtration. Next, the deposit was washed with water, and dried, then purified by means of a silica gel column chromatography (silica gel was the same as defined above; eluant:chloroform:methanol=98:2), there was obtained the above-mentioned desired compound (0.25 g).

Melting point: 200–203° C.; $^1$H-NMR (DMSO-d$_6$) δ: 4.48 (d, J=5.6 Hz, 2H), 5.70 (t, J=5.9 Hz, 1H), 5.85 (s, 1H), 7.30–7.42 (m, 7H), 7.59 (d, J=8.25 Hz, 2H), 8.16 (s, 1H), 11.8 (brs, 1H).

Example 11

[Synthesis of 4,7-dihydro-7-oxo-3-(4-phenylthiphenyl)-5-(tetrahydopyran-4-yloxymethyl)pyrazolo[1,5-a]pyrimidine]

Reactions were carried out similar to those of used in Example 1, except that the same molar quantity of ethyl 4-(tetrahydropyran-4-yloxy)acetoacetate, obtained in Reference Example 20, was used in place of methyl 4-methoxyacetoacetate, there was obtained the above-mentioned desired compound.

Melting point: 213–218° C.; $^1$H-NMR (DMSO-d$_6$) δ: 1.41–1.55 (m, 2H), 1.88–1.92 (m, 2H), 3.31–3.38 (m, 2H), 3.62–3.69 (m, 1H), 3.79–3.86 (m, 2H), 4.53 (s, 2H), 5.86 (s, 1H), 7.30–7.43 (m, 7H), 7.57 (d, J=7.9 Hz, 2H), 8.17 (s, 1H), 11.96 (s, 1H).

Example 12

[Synthesis of 4,7-dihydro-7-oxo-5-phenoxymethyl-3-(4-phenylthiophenyl)pyrazolo[1,5-a]pyrimidine]

Reactions were carried out similar to those of used in Example 1, except that the same molar quantity of ethyl 4-phenoxyacetoacetate was used in place of methyl 4-methoxy-acetoacetate, there was obtained the above-mentioned desired compound.

Melting point: 176–178° C.; $^1$H-NMR (DMSO-d$_6$) δ: 5.12 (s, 2H), 5.92 (s, 1H), 6.98–7.06 (m, 3H), 7.31–7.44 (m, 9H), 7.61 (d, J=8.25 Hz, 2H), 8.20 (s, 1H), 12.2 (s, 1H).

Example 13

[Synthesis of 4,7-dihydro-7-oxo-3-(4-phenylthiophenyl)-5-(3-pyridyloxymethyl)pyrazolo[1,5-a]pyrimidine]

Reactions were carried out similar to those of used in Example 1, except that the same molar quantity of ethyl 4-(3-pyridyloxy)acetoacetate was used in place of methyl 4-methoxyacetoacetate, there was obtained the above-mentioned desired compound.

Melting point: 214–220° C. (decomposed); $^1$H-NMR (DMSO-d$_6$) δ: 5.19 (s, 2H), 5.95 (s, 1H), 7.3–7.6 (m, 9H), 7.62 (d, J=8.25 Hz, 2H), 8.21–8.25 (m, 2H), 8.42 (d, J=2.97 Hz, 1H), 12.2 (brs, 1H).

Example 14

[Synthesis of 4,7-dihydro-5-(2-methoxyethoxymethyl)-7-oxo-3-(4-phenylthiophenyl)pyrazolo[1,5-a]pyrimidine]

Reactions were carried out similar to those of used in Example 1, except that the same molar quantity of ethyl 4-(2-methoxyethoxy)acetoacetate was used in place of methyl 4-methoxyacetoacetate, there was obtained the above-mentioned desired compound.

Melting point: 142–144° C.; $^1$H-NMR (DMSO-d$_6$) δ: 3.26 (s, 3H), 3.49–3.53 (m, 2H), 3.67 (m, 2H), 4.51 (s, 2H), 5.85 (s, 1H), 7.32–7.42 (m, 7H), 7.58 (d, J=8.3 Hz, 2H), 8.17 (s, 1H), 11.94 (s, 1H).

Example 15

[Synthesis of 5-(2-t-butoxyethoxymethyl)-4,7-dihydro-7-oxo-3-(4-phenylthiophenyl)pyrazolo[1,5-a]pyrimidine]

Reactions were carried out similar to those of used in Example 1, except that the same molar quantity of ethyl 4-(2-t-butoxyethoxy)acetoacetate, which was obtained in Reference Example 21, was used in place of methyl 4-methoxyacetoacetate, there was obtained the above-mentioned desired compound.

Melting point: 167–168° C.; $^1$H-NMR (DMSO-d$_6$) δ: 1.13 (s, 9H), 3.47–3.50 (m, 2H), 3.58–3.62 (m, 2H), 4.51 (s, 2H), 5.90 (s, 1H), 7.32–7.42 (m, 7H), 7.57 (d, J=8.3 Hz, 2H), 8.16 (s, 1H), 11.93 (s, 1H).

Example 16

[Synthesis of 4,7-dihydro-5-(2-hydroxyethoxymethyl)-7-oxo-3-(4-phenylthiophenyl)pyrazolo-[1,5-a]pyrimidine]

5-(2-t-Butoxyethoxymethyl-4,7-dihydro-7-oxo-3-(4-phenylthiophenyl)pyrazolo[1,5-a]pyrimidine (450 mg), which was obtained in Example 15, was dissolved in trifluoroacetic acid (4 ml) and this solution was stirred at room temperature. After 26 hours, this solution was neutralized with an aqueous solution of 2N-sodium hydroxide. The formed precipitates were collected by filtration, and washed with water and dried, these was obtain the above-mentioned desired compound (380 mg).

Melting point: 189–194° C.; $^1$H-NMR (DMSO-d$_6$) δ: 3.57 (s, 4H), 4.52 (s, 2H), 4.78 (brs, 1H), 5.90 (s, 1H), 7.30–7.43 (m, 7H), 7.58 (d, J=8.3 Hz, 2H), 8.17 (s, 1H), 11.92 (s, 1H).

Example 17

[Synthesis of 4,7-dihydro-5-(3-methoxypropoxymethyl)-7-oxo-3-(4-phenylthiophenyl)pyrazolo-[1,5-a]pyrimidine]

Reactions were carried out similar to those of used in Example 5, except that the same molar quantity of ethyl 4-(3-methoxypropoxy)acetoacetate, which was obtained in Reference Example 22, was used in place of ethyl 4-isopropoxyacetoacetate, there was obtained the above-mentioned desired compound.

Melting point: 156–158° C.; $^1$H-NMR (CDCl$_3$) δ: 1.86–1.95 (m, 2H), 3.18 (s, 3H), 3.48 (t, J=6 Hz, 2H), 3.70

(t, J=6 Hz, 2H), 4.59 (s, 2H), 5.78 (s, 1H), 7.23–7.34 (m, 9H), 7.91 (s, 1H), 10.21 (brs, 1H).

Example 18
[Synthesis of 4,7-dihydro-5-(3-ethoxypropoxymethyl)-7-oxo-3-(4-phenylthiophenyl)pyrazolo[1,5-a]pyrimidine]

Reactions were carried out similar to those of used in Example 5, except that the same molar quantity of ethyl 4-(3-ethoxypropoxy)acetoacetate, which was obtained in Reference Example 23, was used in place of ethyl 4-isopropoxyacetoacetate, there was obtained the above-mentioned desired compound.

Melting point: 132–134° C.; $^1$H-NMR (CDCl$_3$) δ: 1.11 (t, J=7 Hz, 3H), 1.87–1.96 (m, 2H), 3.39 (q, J=7 Hz, 2H), 3.52 (t, J=6 Hz, 2H), 3.71 (t, J=6 Hz, 2H), 4.61 (s, 2H), 5.80 (s, 1H), 7.20–7.32 (m, 9H), 7.86 (s, 1H), 10.36 (brs, 1H).

Example 19
[Synthesis of 4,7-dihydro-7-oxo-3-(4-phenylthiophenyl)-5-(tetrahydrofuran-2-yl)pyrazolo[1,5-a]pyrimidine]

Reactions were carried out similar to those of used in Example 5, except that the same molar quantity of 4-nitrobenzyl β-oxo-tetrahydro-2-franpropionate, which was obtained in Reference Example 3, was used in place of ethyl 4-isopropoxyacetoacetate, there was obtained the above-mentioned desired compound.

Melting point: 104–108° C.; $^1$H-NMR (CDCl$_3$) δ: 1.98–2.13 (m, 3H), 2.45–2.54 (m, 1H), 3.97–4.14 (m, 2H), 4.93–4.98 (m, 1H), 5.73 (s, 1H), 7.30–7.43 (m, 9H), 8.02 (s, 1H), 9.29 (brs, 1H).

Example 20
[Synthesis of 4,7-dihydro-7-oxo-3-(4-phenylthiophenyl)-5-(tetrahydropyran-2-yl)pyrazolo[1,5-a]pyrimidine]

Reactions were carried out similar to those of used in Example 1, except that the same molar quantity of 4-nitrobenzyl β-oxo-tetrahydro-2-pyranpropionate, which was obtained in Reference Example 4, was used in place of methyl 4-methoxyacetoacetate, there was obtained the above-mentioned desired compound.

Melting point: 209–211° C.; $^1$H-NMR (DMSO-d$_6$) δ: 1.44–1.56 (m, 4H), 1.87–1.99 (m, 2H), 3.36–3.52 (m, 1H), 4.02–4.08 (m, 1H), 4.41 (d, J=10 Hz, 1H), 5.76 (s, 1H), 7.33–7.43 (m, 7H), 7.55 (d, J=7.9 Hz, 2H), 8.14 (s, 1H), 11.81 (s, 1H).

Example 21
[Synthesis of 4,7-dihydro-5-(2-ethoxyethyl)-7-oxo-3-(4-phenylthiophenyl)pyrazolo[1,5-a]pyrimidine]

Reactions were carried out similar to those of used in Example 5, except that the same molar quantity of 4-nitrobenzyl 5-ethoxy-3-oxopentanate, which was obtained in Reference Example 5, was used in place of ethyl 4-isopropoxyacetoacetate, there was obtained the above-mentioned desired compound.

Melting point: 142–143° C.; $^1$H-NMR (CDCl$_3$) δ: 1.63 (t, J=7 Hz, 3H), 2.92 (t, J=5.3 Hz, 2H), 3.58 (q, J=7 Hz, 2H), 3.83 (t, J=5.3 Hz, 2H), 5.71 (s, 1H), 7.26–7.41 (m, 9H), 8.02 (s, 1H), 10.33 (brs, 1H).

Example 22
[Synthesis of 4,7-dihydro-5-(2-methoxyethyl)-7-oxo-3-(4-phenylthiophenyl)pyrazolo[1,5-a]pyrimidine]

Reactions were carried out similar to those of used in Example 5, except that the same molar quantity of 4-nitrobenzyl 5-methoxy-3-oxopentanate, which was obtained in Reference Example 6, was used in place of ethyl 4-isopropoxyacetoacetate, there was obtained the above-mentioned desired compound.

Melting point: 178–181° C.; $^1$H-NMR (CDCl$_3$) δ: 2.93 (t, J=5.3 Hz, 2H), 3.47 (s, 3H), 3.83 (t, J=5.3 Hz, 2H), 5.70 (s, 1H), 7.26–7.42 (m, 9H), 8.02 (s, 1H), 10.43 (brs, 1H).

Example 23
[Synthesis of 4,7-dihydro-5-(3-methoxypropyl)-7-oxo-3-(4-phenylthiophenyl)pyrazolo[1,5-a]pyrimidine]

Reactions were carried out similar to those of used in Example 5, except that the same molar quantity of 4-nitrobenzyl 6-methoxy-3-oxohexanate, which was obtained in Reference Example 7, was used in place of ethyl 4-isopropoxyacetoacetate, there was obtained the above-mentioned desired compound.

Melting point: 183–184° C.; $^1$H-NMR (CDCl$_3$) δ: 1.99–2.08 (m, 2H), 2.85 (t, J=6.3 Hz, 2H), 3.28 (s, 3H), 3.52 (t, J=5.6 Hz, 2H), 5.66 (s, 1H), 7.23–7.36 (m, 9H), 7.88 (s, 1H), 11.24 (brs, 1H).

Example 24
[Synthesis of 4,7-dihydro-5-dimethoxymethyl-7-oxo-3-(4-phenylthiophenyl)pyrazolo[1,5-a]pyrimidine]

A mixture of 3-amino-4-(4-phenylthiophenyl)pyrazole (0.53 g), 4-nitrobenzyl 4,4-dimethoxyacetoacetate (0.71 g), which was obtained in Reference example 8, and acetic acid (4 ml) was stirred at room temperature. After 24 hours, this solution was neutralized with an aqueous solution saturated with sodium hydrogencarbonate, and extracted with ethyl acetate. The organic layer was washed with an aqueous solution saturated with sodium chloride, and dried with anhydrous sodium sulfate and the solvent was removed by distillation. The residue thus obtained was subjected to a silica gel column chromatography (silica gel: the same as defined above, eluate:ethyl acetate:n-hexane=7:3) to separate and purified, there was obtained the above-mentioned desired compound (0.39 g).

Melting point: 157–163° C.; $^1$H-NMR (DMSO-d$_6$) δ: 3.44 (s, 6H), 5.40 (s, 1H), 6.00 (s, 1H), 7.30–7.44 (m, 9H), 8.01 (s, 1H), 9.04 (brs, 1H).

Example 25
[Synthesis of 5-diethoxymethyl-4,7-dihydro-7-oxo-3-(4-phenylthiophenyl)pyrazolo[1,5-a]pyrimidine]

Reactions were carried out similar to those of used in Example 24, except that the same molar quantity of 4-nitrobenzyl 4,4-diethoxyacetoacetate, which was obtained in Reference Example 9, was used in place of 4-nitrobenzyl 4,4-dimethoxyacetoacetate, there was obtained the above-mentioned desired compound.

Melting point: 170–183° C. (decomposed); $^1$H-NMR (CDCl$_3$) δ: 1.19 (t, J=6.93 Hz, 6H), 3.56–3.68 (m, 4H), 5.50 (s, 1H), 5.88 (s, 1H), 7.31–7.44 (m, 7H), 7.56 (d, J=8.25 Hz, 2H), 8.18 (s, 1H), 12.1 (brs, 1H).

Example 26
[Synthesis of 4,7-dihydro-5-(2,2-dimethoxyethyl)-7-oxo-3-(4-phenylthiophenyl)pyrazolo[1,5-a]-pyrimidine]

Reactions were carried out similar to those of used in Example 24, except that the same molar quantity of 4-nitrobenzyl 5,5-dimethoxy-3-oxopentanate, which was obtained in Reference Example 10, was used in place of 4-nitrobenzyl 4,4-dimethoxyacetoacetate, there was obtained the above-mentioned desired compound.

Melting point: 175–178° C.; $^1$H-NMR (CDCl$_3$) δ: 2.99 (d, J=4.62 Hz, 2H), 3.47 (s, 6H), 4.74 (t, J=4.62 Hz, 1H), 5.72 (s, 1H), 7.28–7.40 (m, 9H), 7.99 (s, 1H), 10.2 (brs, 1H).

Example 27
[Synthesis of 4,7-dihydro-5-(2,2-ethylenedioxypropyl)-7-oxo-3-(4-phenylthiophenyl)pyrazolo[1,5-a]pyrimidine]

Reactions were carried out similar to those of use in Example 1, except that the same molar quantity of 4-nitrobenzyl 5,5-ethylenedioxy-3-oxohexanate, which was obtained in Reference Example 11, was used in place of methyl 4-methoxyacetoacetate, there was obtained the above-mentioned desired compound.

Melting point: 199–202° C.; $^1$H-NMR (DMSO-d$_6$) δ: 1.34 (s, 3H), 3.01 (s, 2H), 3.89 (s, 4H), 5.72 (s, 1H), 7.33–7.44 (m, 7H), 7.56 (d, J=7.9 Hz, 2H), 8.16 (s, 1H), 11.7 (brs, 1H).

Example 28

[Synthesis of 4,7-dihydro-5-(3,3-ethylenedioxybutyl)-7-oxo-3-(4-phenylthiophenyl)pyrazolo[1,5-a]pyrimidine]

Reactions were carried out similar to those of used in Example 1, except that the same molar quantity of 4-nitrobenzyl 6,6-ethylenedioxy-3-oxoheptanate, which was obtained in Reference Example 12, was used in place of methyl 4-methoxyacetoacetate, there was obtained the above-mentioned desired compound.

Melting point: 192–196° C.; $^1$H-NMR (DMSO-d$_6$) δ: 1.29 (s, 3H), 1.96–2.02 (m, 2H), 2.66–2.73 (m, 2H), 3.90 (s, 4H), 5.69 (s, 1H), 7.33–7.43 (m, 7H), 7.58 (d, J=8.25 Hz, 2H), 8.12 (s, 1H), 11.8 (brs, 1H).

Example 29

[Synthesis of 4,7-dihydro-5-methylthiomethyl-7-oxo-3-(4-phenylthiophenyl)pyrazolo[1,5-a]pyrimidine]

Reactions were carried out similar to those of used in Example 1, except that the same molar quantity of 4-nitrobenzyl 4-methylthioacetoacetate, which was obtained in Reference Example 13, was used in place of methyl 4-methoxyacetoacetate, there was obtained the above-mentioned desired compound.

Melting point: 221–224° C.; $^1$H-NMR (DMSO-d$_6$) δ: 2.10 (s, 3H), 3.70 (s, 2H), 5.82 (s, 1H), 7.33–7.44 (m, 7H), 7.57 (d, J=8.25 Hz, 2H), 8.17 (s, 1H), 11.9 (brs, 1H).

Example 30

[Synthesis of 4,7-dihydro-5-ethylthiomethyl-7-oxo-3-(4-phenylthiophenyl)pyrazolo[1,5-a]pyrimidine]

Reactions were carried out similar to those of used in Example 1, except that the same molar quantity of 4-nitrobenzyl 4-ethylthioacetoacetate, which was obtained in Reference Example 14, was used in place of methyl 4-methoxyacetoacetate, there was obtained the above-mentioned desired compound.

Melting point: 207–210° C.; $^1$H-NMR (CDCl$_3$) δ: 1.26 (t, J=7.3 Hz, 3H), 2.55 (q, J=7.3 Hz, 2H), 3.78 (s, 2H), 5.80 (s, 1H), 7.29–7.37 (m, 9H), 7.96 (s, 1H), 9.97 (brs, 1H).

Example 31

[Synthesis of 4,7-dihydro-7-oxo-3-(4-phenylthiophenyl)-5-(2-pyridylthiomethyl)pyrazolo[1,5-a]pyrimidine]

Reactions were carried out similar to those of used in Example 1, except that the same molar quantity of ethyl 4-(2-pyridylthio)acetoacetate, which was obtained in Reference Example 24, was used in place of methyl 4-methoxyacetoacetate, there was obtained the above-mentioned desired compound.

Melting point: 222–224° C.; $^1$H-NMR (DMSO-d$_6$) δ: 4.40 (s, 2H), 5.89 (s, 1H), 7.17 (dd, J=5 Hz, 7 Hz, 1H), 7.31–7.45 (m, 8H), 7.57 (d, J=8.25 Hz, 2H), 7.71 (dt, J=2 Hz, 8 Hz, 1H), 8.18 (s, 1H), 8.44 (d, J=5 Hz, 1H), 12.2 (brs, 1H).

Example 32

[Synthesis of 4,7-dihydro-5-(2-methylthioethyl)-7-oxo-3-(4-phenylthiophenyl)pyrazolo[1,5-a]pyrimidine]

Reactions were carried out similar to those of used in Example 1, except that the same molar quantity of 4-nitrobenzyl 5-methylthio-3-oxopentanate, which was obtained in Reference Example 15, was used in place of methyl 4-methoxyacetoacetate, there was obtained the above-mentioned desired compound.

Melting point: 202–204° C.; $^1$H-NMR (DMSO-d$_6$) δ: 2.12 (s, 3H), 2.83–2.91 (m, 4H), 5.79 (s, 1H), 7.33–7.42 (m, 7H), 7.58 (d, J=7.59 Hz, 2H), 8.14 (s, 1H), 11.8 (brs. 1H).

Example 33

[Synthesis of 4,7-dihydro-7-oxo-3-(4-phenylthiophenyl)-5-[2-(2-pyridylthio)ethyl]pyrazolo[1,5-a]pyrimidine]

Reactions were carried out similar to those of used in Example 1, except that the same molar quantity of 4-nitrobenzyl 5-(2-pyridylthio)-3-oxopentanate, which was obtained in Reference Example 16, was used in place of methyl 4-methoxyacetoacetate, there was obtained the above-mentioned desired compound.

Melting point: 193–197° C.; $^1$H-NMR (DMSO-d$_6$) δ: 3.03 (t, J=7 Hz, 2H), 3.53 (t, J=7 Hz, 2H), 5.74 (s, 1H), 7.06–7.11 (m, 1H), 7.30–7.42 (m, 8H), 7.57–7.65 (m, 3H), 8.14 (s, 1H), 8.38 (d, J=4.65 Hz, 1H), 11.9 (brs, 1H).

Example 34

[Synthesis of 4,7-dihydro-5-(3-ethylthiopropyl)-7-oxo-3-(4-phenylthiophenyl)pyrazolo[1,5-a]pyrimidine]

Reactions were carried out similar to those of used in Example 1, except that the same molar quantity of 4-nitrobenzyl 6-ethylthio-3-oxohexanate, which was obtained in Reference Example 17, was used in place of methyl 4-methoxyacetoacetate, there was obtained the above-mentioned desired compound.

Melting point: 173–176° C.; $^1$H-NMR (CDCl$_3$) δ: 1.17 (t, J=7.3 Hz, 3H), 2.06 (m, 2H), 2.46 (q, J=7.3 Hz, 2H), 2.61 (t, J=7 Hz, 2H), 2.87 (t, J=7 Hz, 2H), 5.66 (s, 1H), 7.17–7.32 (m, 9H), 7.83 (s, 1H), 10.7 (brs, 1H).

Example 35

[Synthesis of sodium 5-methoxymethyl-3-(4-phenylthiophenyl)pyrazolo[1,5-a]pyrimidin-7-olate]

4,7-Dihydro-5-methoxymethyl-7-oxo-3-(4-phenylthiophenyl)pyrazolo[1,5-a]pyrimidine (0.98 g), which was obtained in Example 1, was dissolved in ethyl alcohol (20 ml) and an aqueous solution of 1N-sodium hydroxide (2.7 ml), then the solution was concentrated under reduced pressure, the residue thus obtained was dried, there was obtained the above-mentioned desired compound (1.04 g).

Melting point: 206–209° C.; $^1$H-NMR (DMSO-d$_6$) δ: 3.36 (s, 3H), 4.31 (s, 2H), 5.66 (s, 1H), 7.20–7.40 (m, 7H), 8.19–8.22 (m, 3H).

Example 36

[Synthesis of 4,7-dihydro-5-methoxymethyl-3-(3-methyl-4-phenylthiophenyl)-7-oxopyrazolo[1,5-a]pyrimidine]

Reactions were carried out similar to those of used in Example 5, except that methyl 4-methoxyacetate was used in place of ethyl 4-isopropoxyacetate, and the same molar quantity of 3-amino-4-(3-methyl-4-phenylthiophenyl)pyrazole, which was disclosed in WO 92/06096, was used in place of 3-amino-4-(4-phenylthiophenyl)pyrazole, there was obtained the above-mentioned desired compound.

Melting point: 151–157° C.; $^1$H-NMR (CDCl$_3$) δ: 2.42 (s, 3H), 3.53 (s, 3H), 4.50 (s, 2H), 5.76 (s, 1H), 7.17 (d, J=7.6 Hz, 1H), 7.22–7.35 (m, 7H), 8.02 (s, 1H), 9.16 (brs, 1H).

Example 37

[Synthesis of 4,7-dihydro-5-methoxymethyl-3-(3-methoxy-4-phenylthiophenyl)-7-oxopyrazolo[1,5-a]pyrimidine]

Reactions were carried out similar to those of used in Example 1, except that the same molar quantity of 3-amino-4-(3-methoxy-4-phenylthiophenyl)pyrazole, which was disclosed in WO 92/06096, was used in place of 3-amino-4-(4-phenylthiophenyl)pyrazole, there was obtained the above-mentioned desired compound.

Melting point: 194–197° C.; $^1$H-NMR (CDCl$_3$) δ: 3.52 (s, 3H), 3.91 (s, 3H), 4.52 (s, 2H), 5.75 (s, 1H), 6.85–6.91 (m, 2H), 7.06 (d, J=7.6 Hz, 1H), 7.26–7.40 (m, 5H), 7.98 (s, 1H), 9.44 (brs, 1H).

Example 38

[Synthesis of 4,7-dihydro-5-(3-methylphenoxymethyl)-7-oxo-3-(4-phenylthiophenyl)pyrazolo[1,5-a]pyrimidine]

Reactions were carried out similar to those of used in Example 1, except that the same molar quantity of ethyl 4-(3-methylphenoxy)acetoacetate, which was obtained in Reference Example 25, was used in place of methyl 4-methoxyacetoacetate, there was obtained the above-mentioned desired compound.

Melting point: 188–190° C.; $^1$H-NMR (CDCl$_3$) δ: 2.31 (s, 3H), 5.18 (s, 2H), 5.92 (s, 1H), 6.75–6.85 (m, 3H), 7.14–7.28 (m, 10H), 7.85 (s, 1H), 10.7 (brs, 1H).

Example 39

[Synthesis of 4,7-dihydro-7-oxo-3-(4-phenylthiophenyl)-5-(3-trifluoromethylphenoxymethyl)pyrazolo[1,5-a]pyrimidine]

Reactions were carried out similar to those of used in Example 5, except that the same molar quantity of ethyl 4-(3-trifluoromethylphenoxy)acetoacetate, which was obtained in Reference Example 26, was used in place of ethyl 4-isopropoxyacetoacetate, there was obtained the above-mentioned desired compound.

Melting point: 173–176° C.; $^1$H-NMR (CDCl$_3$) δ: 5.29 (brs, 1H), 5.95 (brs, 1H), 7.10–7.42 (m, 13H), 7.78 (brs, 1H), 11.4 (brs, 1H).

Example 40

[Synthesis of 4,7-dihydro-5-(3-methoxyphenoxymethyl)-7-oxo-3-(4-phenylthiophenyl)pyrazolo[1,5-a]pyrimidine]

Reactions were carried out similar to those of used in Example 1, except that the same molar quantity of 4-(3-methoxyphenoxy)acetoacetate, which was obtained in Reference Example 27, was used in place of methyl 4-methoxyacetoacetate, there was obtained the above-mentioned desired compound.

Melting point: 191–194° C.; $^1$H-NMR (CDCl$_3$) δ: 3.76 (s, 3H), 5.17 (s, 2H), 5.92 (s, 1H), 6.53–6.58 (m, 3H), 7.16–7.28 (m, 10H), 7.86 (s, 10H), 10.6 (br, 1H).

Example 41

[Synthesis of 5-(4-carboxyphenoxymethyl)-4,7-dihydro-7-oxo-3-(4-phenylthiophenyl)pyrazolo[1,5-a]pyrimidine]

Reactions were carried out similar to those of used in Example 1, except that the same molar quantity of ethyl 4-(4-carboxyphenoxy)acetoacetate, which was obtained in Reference Example 28, was used in place of methyl 4-methoxyacetoacetate, there was obtained the above-mentioned desired compound.

Melting point: >300° C. (decomposed); $^1$H-NMR (CDCl$_3$) δ: 5.19 (s, 2H), 5.93 (s, 1H), 7.13 (d, J=8 Hz, 2H), 7.30–7.44 (m, 7H), 7.61 (d, J=8 Hz, 2H), 7.93 (d, J=8 Hz, 2H), 8.21 (s, 1H), 12.2 (brs, 1H), 12.7 (br, 1H).

Example 42

[Synthesis of 2,5-bis(methoxymethyl)-4,7-dihydro-7-oxo-3-(4-phenylthiophenyl)pyrazolo[1,5-a]-pyrimidine]

Reactions were carried out similar to those of used in Example 1, except that the same molar quantity of 3-amino-5-methoxymethyl-4-(4-phenylthiophenyl)pyrazole, which was disclosed in WO 92/06096, was used in place of 3-amino-4-(4-phenylthiophenyl)pyrazole, there was obtained the above-mentioned desired compound.

Melting point: 192–198° C.; $^1$H-NMR (CDCl$_3$) δ: 3.38 (s, 3H), 3.50 (s, 3H), 4.47 (s, 2H), 4.55 (s, 2H), 5.74 (s, 1H), 7.32–7.46 (m, 9H), 9.05 (brs, 1H).

The present invention will be explained more specifically by showing Pharmacological Tests and Preparation Examples below.

PHARMACOLOGICAL TESTS

Test Example 1

[Evaluation test of activity for inhibiting the formation of NO]

Pharmacological tests of pyrimidine derivatives obtained in Examples 1, 12, 14, 19, 22, 24, 29 and 42 used as test compounds were conducted as follows.

Preparation of culture media and method of cell culture were conducted in accordance with those described in J. Biol. Chem., Vol. 269, No. 1, pp. 711–715, (1994), and determination of formed amount of NO was conducted in accordance with the method described in Anal. Biochem., Vol. 126, pp. 131–138, (1982), respectively.

(1) Cell Culture and Inducible Synthesis of NO in the Cells by Stimulation with Lipopolysaccharide (LPS)

Cell strain RAW 264.7 (ATCC) derived from the macrophage of mouse was placed on each one of the wells on a microplate having 24-wells so as to put the cells in an amount of 1×10$^5$ cells/U (well). The cells were incubated for 24 hours in a phenol red free-RPMI-1640 culture medium (mfd. by GIBCO) to which 10% of fetal bovine serum, 100 U/ml of penicillin (mfd. by Dainippon Pharmaceutical Co., Ltd.) and 100 μg/ml of streptomycin (mfd. by Dainippon Pharmaceutical Co., Ltd.) were added.

Next, the reference culture medium was prepared by adding 2 mM of L-arginine (mfd. by Wako Pure Chemical Industries, Ltd.), 10 μM/ml of tetrahydrobiopterin (mfd. by ALEXIS) and 100 ng/ml of lipopolysaccharide (LPS)(mfd. by Sigma Chemical Co.) to a phenol red free-RPMI-1640 culture medium. While, the reference culture medium without containing LPS was used as the blanc culture medium.

On the other hand, the test culture medium, containing the test compound was prepared by adding 0.2% of the test compounds dissolved in dimethyl sulfoxide (DMSO) to the reference culture medium to adjust the final concentration of the test compound to 1×10$^{-6}$ M.

Each one of the blank culture medium, reference culture medium and test culture medium containing the test compound was added, respectively to the well on the micro-plate where the above-mentioned cell strain RAW 264.7 was placed, and was incubated for 24 hours.

(2) Measurement of the Amount of Formed NO

Quantitative measurement of NO cannot be made directly, due to its unstability. Therefore, the amount of NO is measured indirectly, thus by forming nitrous acid ion (hereunder referred to as NO$_2^-$) which is stable product derived from NO by use of Griess reagent [consisting of 1% of sulfanylamide and 0.1% of sulfuric acid solution containing 0.1% N-(1-naphthyl)ethylenediamine dihydrochloride], and measure the amount of NO$_2^-$.

Into the supernatant of each one of the culture media was admixed with the same amount of Griess reagent respectively, and subjected to reaction at room temperature for 10 minutes, then the optical absorbance at 540 nm of the thus reacted culture medium was measured. While, the optical absorbance of sodium nitrite solution diluted with the culture medium was referred to as the standard value, and the amount of $NO_2^-$ formed in each one of these incubated culture media was measured. The amounts of $NO_2^-$ formed in the reference culture medium and the test culture medium were corrected by using the value of formed amount of $NO_2^-$ in the blanc culture medium.

On the basis of that the ratio of amounts of $NO_2^-$ formed in the reference culture medium and that of formed in the test culture medium is corresponding to the ratio of amount of NO formed in the reference culture medium and that of formed in the test culture medium. Thus the amount of $NO_2^-$ formed in the reference culture medium is referred to as the value of 100, and the value of amount of $NO_2^-$ formed in the test culture medium is referred to as amount of NO formed in the test culture medium. The results are shown in the following Table 1.

TABLE 1

| Test compound | Ratio of formed amount of NO (%) (*) |
|---|---|
| Example 1 | 56.0 |
| Example 12 | 67.0 |
| Example 14 | 64.4 |
| Example 19 | 63.1 |
| Example 22 | 60.3 |
| Example 24 | 67.3 |
| Example 29 | 52.2 |
| Example 42 | 55.4 |

(*) Measured at the concentration of $1 \times 10^{-6}$ M of the test compound.

Test Example 2
[Toxicity test (Toxicity of compound against the cell strain RAW 264.7)]

Test was conducted in accordance with the method as described in J. Immunol. Methods, Vol. 94, pp. 57–68, (1986). Cell strain RAW 264.7 derived from the macrophage of mouse was incubated similarly as in the method of Test Example 1(1). After that, MTT reagent (5 mg/ml) in 1/10 amount of the culture medium was added to the cells, and incubated for 4 hours. The supernatant of culture medium was taken off, then the cells were collected by using 1% SDS solution and the optical absorbance at 570–630 nm of the SDS solution was measured. The results are shown in the following Table 2.

TABLE 2

| Test compound | Ratio of optical absorbance (%) (**) |
|---|---|
| Example 1 | 108.9 |
| Example 12 | 102.8 |
| Example 14 | 94.2 |
| Example 22 | 101.2 |
| Example 24 | 107.7 |
| Example 29 | 89.7 |

(**) Measured at the concentration of $1 \times 10^{-6}$ M of the test compound.

Test Example 3
[Model experiment of asthma in guinea pigs. (Inhibition of late asthmatic response)]

Test was conducted by the method described in J. Pharmacol. Exp. Ther., Vol. 277, pp. 1622–1629, (1996).

Hartley strain female guinea pigs (SLC) having the body weight of about 350 g were used and 50 mg/Kg of cyclophosphamide (mfd. by Sigma Chemical Co.) was injected intraperitoneally. 2 Days after this pretreatment by injection, 1 mg of egg albumin (mfd. by Sigma Chemical Co.) and 100 mg of aluminum hydroxide (Wako Pure Chemical Industries Co., Ltd.) were injected intraperitoneally for sensitization. 3 Weeks after the sensitization, 10 µg of egg albumin and 100 mg of aluminum hydroxide were injected intraperitoneally for booster sensitization. 6 Weeks after the primary sensitization, asthma attach was induced by inhalation and exposure to egg albumin (4 mg/ml) by using a nebulizer (NE-U12: mfd. by Omron Corp.). The asthma reaction was determined by use of a body-plethysmography (using system developed by Uchida lecturer in internal department for respiratory organs at Tsukuba University; air-resist tube, respiratory amplifier and differential pressure transducer (mfd. by Nihon Koden); and osciloscope (mfd. by Iwasaki Tsushin)), so as to determine a drug of specific airway conductance (sGaw) under the condition without anesthesia. The sGaw value just before the administration of test comopound was measured and the value is referred to as 100. Test compound was suspended in 1% HPMC (hydroxymethylpropylcellulose mfd. by Shinetsu Chemical), and was administered orally 30 minutes before the exposure with the antigen. Then, sGaw value was measured in each points until 7 hours after the exposure with the antigen. Effect of the test compound was evaluated from the area under curve (AUC) of sGaw reaction induced by the exposure with the antigen during 4–7 hours. The results are shown in the following Table 3.

TABLE 3

| Test compound (mg/Kg of body weight) | | Number of test animals | AUC (4–7 hours) |
|---|---|---|---|
| Control | (10) | 6 | 112 ± 17.8 |
| Compound of Example 1 | (10) | 6 | 32.8 ± 9.2 |
| Prednizolone | (30) | 8 | 15.6 ± 3.5 |
| 7-Hydroxy-3-(4-phenylthio-phenyl)pyrazolo[1,5-a]-pyrimidine (Exp. 3 of JP-A-5-112571) | (39) | 3 | 127.9 ± 45.4 |

Test Example 4
[Contact hypersensitivity model in mouse (Atopic dermatisis model)]

Test was conducted by referring to the method as described in "HIFU (a Japanese journal of dermatology)" Vol. 35, Supplemental Issue No. 15, pp. 96–106, published on March 1993.

CBA/J strain mice of 6–8 week age were used as the test animals (6–8 mice in one group). The mouse was sensitized by coating 150 µl of 5% of picryl chloride [dissolved in a mixture of acetone with olive oil (1:4)] on the shaved portion of skin in the back of mouse. 4 Days after the sensitization, contact hypersensitivity was causally induced by coating 0.8%, 5% of picryl chloride [dissolved in a mixture of acetone with olive oil (1:4)] on the left-pinna of the mouse. 24 Hours after the causal induction, the effect for inhibiting contact hypersensitivity performed by the test compounds were evaluated by referring to the action for inhibiting intumescence of the pinna as an indication. The test compound was orally administered 30 minutes before the causal induction.

The following compounds were used for the test.
1) Compounds of the Present Invention:
 (1) Compound of Example 1 (Dosage: 2 mg/Kg p.o.)
 (2) Compound of Example 15 (Dosage: 3 mg/Kg p.o.)
 (3) Compound of Example 19 (Dosage: 3 mg/Kg p.o.)

2) Comparative Compounds
(Dosage: 20 mg/Kg p.o., which is 7–10 times larger amount of dosages for compounds of the present invention)
(1) 7-Hydroxy-5-cyclopropyl-3-(4-phenylthiophenyl) pyrazolo[1,5-a]pyrimidine (Example 8 of JP-A-5-112571 and Example 7 of WO97/11946)
(2) 7-Hydroxy-5-methyl-3-(4-phenylthiophenyl)pyrazolo [1,5-a]pyrimidine (Example 5 of JP-A-5-112571)
(3) 7-Hydroxy-2-methoxymethyl-3-(4-phenylthiophenyl) pyrazolo[1,5-a]pyrimidine (Example 19 of JP-A-5-112571)
(4) 7-Hydroxy-5-chloromethyl-2-phenylpyrazolo[1,5-a] pyrimidine (Example 29 of WO97/11946)
(5) 7-Hydroxy-3-(3-trifluoromethylphenyl)pyrazolo [1,5-a]pyrimidine (Example 27 of WO97/11946)
(6) 7-Hydroxy-5-methyl-3-(3-methoxy-4-phenylthiophenyl)-2-(2-pyridyl)pyrazolo[1,5-a] pyrimidine (Example 31 of WO97/11946)
(7) 7-Hydroxy-5-chloromethyl-2-(4-phenylthiophenyl) pyrazolo[1,5-a]pyrimidine (Example 33 of WO97/11946)
(8) 7-Hydroxy-3-(4-phenylthiophenyl)pyrazolo[1,5-a] pyrimidine (Example 3 of JP-A-5-112571)

The value obtained from the sensitization test without administration of the test compound was referred to as 100, and by comparing with the values obtained from the sensitization test with administration of the test compound was referred to "% control" values. The results are shown in the following Table 4.

TABLE 4

| Test compound | Control % |
|---|---|
| 1) Compound of the present invention | |
| (1) | 53.7 |
| (2) | 46.3 |
| (3) | 44.7 |
| 2) Comparative compounds | |
| (1) | 99.0 |
| (2) | 90.0 |
| (3) | 104.2 |
| (4) | 102.6 |
| (5) | 90.4 |
| (6) | 94.7 |
| (7) | 113.0 |
| (8) | 100.0 |

Test Example 5
[Evaluation test of activity for inhibiting the formation of TNF-α in vitro]

Pyrimidine derivative obtained in Example 1 was used as test compound.

Cell strain RAW 264.7 (ATCC) derived from the macrophage of mouse was placed on each one of the wells on a microplate having 24-wells so as to put the cells in an amount of $3 \times 10^5$ cells/U (well). The cells were incubated for 24 hours in a phenol red free-RPMI-1640 culture medium (mfd. by GIBCO) to which 10% of equine serum (mfd. by Bio Whittaker), 100 U/ml of penicillin (mfd. by Dainippon Pharmaceutical Co., Ltd.) and 100 μg/ml of streptomycin (mfd. by Dainippon Pharmaceutical Co., Ltd.) were added.

Next, the equine serum was removed from the culture medium, and the reference culture medium as control was prepared by adding 2 mM of L-arginine (mfd. by Wako Pure Chemical Industries, Ltd.), 10 μM/ml of tetrahydrobiopterin (mfd. by ALEXIS) and 100 ng/ml of lipopolysaccharide (LPS)(mfd. by Sigma Chemical Co.) to a phenol red free-RPMI-1640 culture medium, so as to induce the formation of TNF-α.

On the other hand, the test culture medium, containing the test compound of Example 1 was prepared similarly as in the reference culture medium, except adding the test compound ($1 \times 10^{-4}$, $1 \times 10^{-5}$ and $1 \times 10^{-6}$ M) dissolved in dimethyl sulfoxide (DMSO) at the same time of LPS-addition.

The concentration of TNF-α formed in the supernatant of each one of the culture media after 24 hour-incubation was measured by Factor-Test-X Mouse TNF-α ELISA Kit (mfd. by genzyme). The results are shown in the following Table 5.

TABLE 5

| Test compound | Concentration (M) | Ratio of formed amount of TNF-α (%) |
|---|---|---|
| Control | — | 100 |
| Example 1 | $1 \times 10^{-6}$ | 120.0 |
| " | $1 \times 10^{-5}$ | 59.9 |
| " | $1 \times 10^{-4}$ | 5.1 |

Test Example 6
[Evaluation test of activity for inhibiting the formation of IL-8 in vitro]

Pyrimidine derivative obtained in Example 1 was used as test comppound.

Cell strain A 549 (ATCC) derived from human alveolar epithelium cells was placed on each one of the wells on a microplate having 24-wells so as to put the cells in an amount of $3 \times 10^5$ cells/U (well). The cells were incubated for 24 hours in F-12 Nutrient Mixture culture medium (mfd. by GIBCO) to which 10% of equine serum, 100 U/ml of penicillin (mfd. by Dainippon Pharmaceutical Co., Ltd.) and 100 μg/ml of streptomycin (mfd. by Dainippon Pharmaceutical Co., Ltd.) were added.

Next, the equine serum was removed from the culture medium, and the reference culture medium as control was prepared by adding inducers of TNF-α (mfd. by genzyme), IL-1β (mfd. by genzyme) and IFN-γ (mfd. by genzyme) to the culture medium, so as to induce the formation of IL-8.

On the other hand, the test culture medium, containing the test compound of Example 1 was prepared similarly as in the reference culture medium, except adding the test compound ($1 \times 10^{-5}$, $1 \times 10^{-6}$ and $1 \times 10^{-7}$ M) dissolved in dimethyl sulfoxide (DMSO) at the same time of inducers-addition.

The concentration of IL-8 formed in the supernatant of each one of the culture media after 24-hour incubation was measured by IL-8 ELISA Kit Human (mfd. by genzyme). Further, MTT assay was conducted by the similar method as described in Text Example 2 to determine the index of toxicity for cells. The results are shown in the following Table 6.

TABLE 6

| Test compound | Concentration (M) | Ratio of formed amount of IL-8 (%) | Ratio of optical absorbance (%) |
|---|---|---|---|
| Control | — | 100.0 | 100.0 |
| Example 1 | $1 \times 10^{-7}$ | 64.5 | 108.2 |

TABLE 6-continued

| Test compound | Concentration (M) | Ratio of formed amount of IL-8 (%) | Ratio of optical absorbance (%) |
|---|---|---|---|
| " | 1 × 10$^{-6}$ | 52.6 | 98.1 |
| " | 1 × 10$^{-5}$ | 13.4 | 126.5 |

Test Example 7

[Evaluation test of activity for inhibiting 5-lipoxygenase in vitro]

Pyrimidine derivative obtained in Example 1 was used as test compound.

Test was referred to the methods as described in Proc. Natl. Acad. Sci. U.S.A., Vol. 81, pp. 689–693 (1984) and J. Biol. Chem., Vol. 260, pp. 11554–11559 (1985).

(1) Preparation of Crude Enzyme Containing 5-lipoxygenase

RBI-1 cells (rat basophilic leukemia-1, ATCC, 1×10$^8$ cells) in 5 ml of buffer solution (50 mM Tris/1 mM EDTA, pH 7.4) were lysed with nitrogen cavitation bomb (mfd. by PARR Instrument Company) under 750 psi for 20 min at 4° C. The solution were centrifuged with twice volume of 50 mM Tris/1 mM EDTA (pH 7.4) at 5000 rpm for 10 minutes at 4° C. The supernatant of the solution was taken and further centrifuged at 37,500 rpm for 90 minutes at 4° C. Thus obtained supernatant was collected and concentrated so as to obtain crude enzyme containing 5-lipoxygenase. Its protein concentration was determined with Protein assey kit (mfd. by Pierce).

(2) Evaluation of Activity for Inhibiting 5-lipoxygenase (RIA assay)

12.5 μl of Crude enzyme, 61.5 μl of 50 mM Tris-HCl (mfd. by Sigma Chemical Co.), 12.5 μl of 0.5 mM ATP (mfd. by Sigma Chemical Co.), and 12.5 μl of cofacter solution (50 mM Tris-HCl (pH 7.2, at 25° C.) containing 10 mM glutahion, 14 mM of indomethacin and 500 mM of CaCl$_2$.2H$_2$O) were preincubated for minutes at 25° C. for reference solution as control. On the other hand, the test solution containing the test compound of Example 1 was prepared similarly as in the reference solution, except adding 1 μl of the test compound (1×10$^{-4}$, 1×10$^{-5}$, and 1×10$^{-6}$ M).

25 μl of 0.07 mM Arachidonic acid (mfd. by Sigma Chemical Co.) was added each of the reference solution and test solutin to intiate the reaction, and incubated it for 8 minutes at 25° C. The reaction was terminated by adding 40 μl of citric acid (mfd. by Sigma Chemical Co.). 350 μl of 0.11 M Butylated hydroxytoluene solution (in 50 mM of Tris-HCl, pH 8.5) was added thereto and each of the mixed solutions were stirred vigorously.

RIA assay was conducted by the 5-HETE [$^3$H] RIA assay kit (mfd. by PerSeptive Biosystems) according to its instructions. 7 μl of each mixed solutions were used as reaction solution for 5-HETE [$^3$H] RIA assay to determine the amount of 5-lipoxygenase by counting radioactivity on the liquid scintillation counter (mfd. by Beckman Co.).

The value obtained from the reference solution as control was compared with that of the test solutions by the rate of "%inhibition". The results are shown in the following Table 7.

TABLE 7

| Test compound | Concentration (M) | % Inhibition |
|---|---|---|
| Example 1 | 1 × 10$^{-6}$ | 68.0 |
| " | 1 × 10$^{-5}$ | 38.8 |
| " | 1 × 10$^{-4}$ | 24.3 |

Preparation Example 1

| | |
|---|---|
| 4,7-Dihydro-5-methoxymethyl-7-oxo-3-(4-phenylthiophenyl)-pyrazolo[1,5-a]pyrimidine | 150 g |
| Avicel (trade name for microcrystalline cellulose, manufactured by Asahi Chemical Industry Co., Ltd.) | 40 g |
| Corn starch | 30 g |
| Magnesium stearate | 2 g |
| Hydroxypropylmethyl cellulose | 10 g |
| Polyethylene glycol 6000 | 3 g |
| Castor oil | 40 g |
| Methanol | 40 g |

4,7-Dihydro-5-methoxymethyl-7-oxo-3-(4-phenylthiophenyl)pyrazolo[1,5-a]pyrimidine, Avicel, corn starch and magnesium stearate were mixed together and ground, then the mixture was shaped into the form of tables by using a conventional pounder (R 10 mm) for sugar coating. The tablets were coated with a film-coating agent consisting of hydroxypropylmethyl cellulose, propylene glycol 6000, caster oil and methanol, to prepare film-coated tablets.

Preparation Example 2

| | |
|---|---|
| 4,7-Dihydro-5-methoxymethyl-7-oxo-3-(4-phenylthiopheyl)pyrazolo-[1,5-a]pyrimidine | 150.0 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | A sufficient quantity |

4,7-Dihydro-5-methoxymethyl-7-oxo-3-(4-phenylthiophenyl)pyrazolo[1,5-a]pyrimidine, citric acid, lactose, dicalcium phosphate, Pluronic F-68 and sodium lauryl sulfate were mixed together.

The mixture was sieved through a No. 60 screen. The resulting sieved mixture was wet-granulated with an ethanol solution containing polyvinyl pyrrolidone, Carbowax 1500 and Carbowax 6000. In case of necessity, ethanol was added to convert the mixture into a paste-like mass. Corn starch was added, and mixing operation was contiued until uniform particles were formed. The resulting particles were passed through a No. 10 screen, then placed in a tray, and were dried in an oven at 100° C. for 12–14 hours. The dried particles were sieved through a No. 16 screen. Next, dry sodium lauryl sulfate and dry magnesium stearate were added to the resulting particles. The mixture was compressed into core tablets of the desired shape by using a tablet machine.

The resulting core tablets were treated with a varnish and then talc was sprayed thereon for preventing from moisture absorption. On the surface of resulting core tablets, undercoat layer was coated. Sufficient number of varnish coatings were conducted to the core tablets so as to make them suitable for internal use. Formation of undercoat layer and smooth coating were conducted to make the coated tablets having completely round and smooth surface. Color coating was conducted until the desired color surface was obtained. After drying, the coated tablets were polished to obtain tablets of uniform gloss.

Preparation Example 3

| | |
|---|---|
| 4,7-Dihydro-5-methoxymethyl-7-oxo-3-(4-phenylthiophenyl)-pyrazolo[1,5-a]pyrimidine | 5.0 g |
| Polyethylene glycol (mol. wt.: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

Parabens, sodium metabisulfite and sodium chloride were dissolved in a half volume of the above mentioned distilled water for injection at 80° C. under stirring. The resulting solution was cooled to 40° C., then to this solution was added 4,7-dihydro-5-methoxymethyl-7-oxo-3-(4-phenylthiophenyl)pyrazole[1,5-a]pyrimidine, polyethylene glycol and polyoxyethylene sorbitan monooleate and were dissolved. Next, to the resulting solution was added the remaining a half volume of the distilled water to make the solution to the final volume. Thus obtained solution was sterilized by passing through a suitable filter paper, to prepare the desired injection preparation.

What is claimed is:

1. A compound represented by the formula (1), (1)

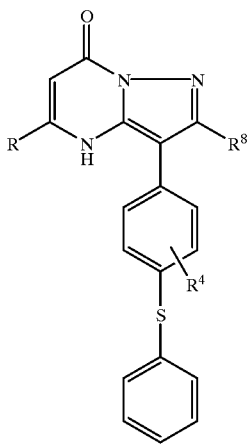

wherein R represents a group of the formula,

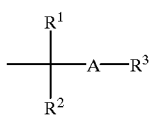

wherein $R^1$ and $R^2$ are a hydrogen atom; $R^3$ is a methyl group and A is an oxygen atom and $R^4$ and $R^8$ a hydrogen atom, or pharmaceutically acceptable salt thereof.

2. A method for treating an allergic disease by administering to a patient in need thereof an agent comprising, as the effective ingredient, a compound represented by the formula (1) or pharmaceutically acceptable salt thereof as claimed in claim 1.

3. A method for treating asthma by administering to a patient in need thereof an agent comprising, as the effective ingredient, a compound represented by the formula (1) or pharmaceutically acceptable salt thereof as claimed in claim 1.

4. A method for treating an atopic dermatitis, by administering to a patient in need thereof an agent comprising, as the effective ingredient, a compound represented by the formula (1) or pharmaceutically acceptable salt thereof as claimed in claim 1.

5. A method for treating an allergic disease, by administering to a patient in need thereof an agent comprising, as the effective ingredient, a compound represented by the formula (1), (1)

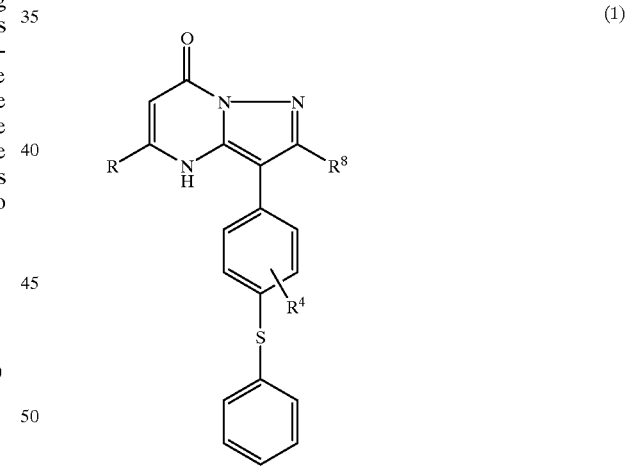

wherein R represents a group of the formula,

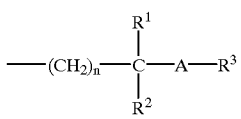

wherein $R^1$ is a hydrogen atom or a lower alkyl group; $R^2$ is a hydrogen atom or a lower alkoxy group; $R^3$ is a hydrogen atom, an alkyl group, a lower alkanoyl group, a phenyl group which may have substituents selected from the group consisting of a lower alkoxy group, a carboxyl group, a halogen substituted-lower alkyl group and a lower alkyl group, an aralkyl group, a tetrahydropyranyl group, a pyridyl group, a cycloalkyl group, a hydroxy-lower alkyl group, and a lower alkoxy-lower alkyl group; A is an oxygen atom or sulfur atom; further $R^2$ and $R^3$ may be combined to each other to form a tetrahydrofuranyl group or tetrahydropyranyl group; n is 0–2; $R^4$ is a hydrogen atom, a lower alkyl group or a lower alkoxy group; $R^8$ is a hydrogen atom, a lower alkyl group or a lower alkoxy-lower alkyl group, or pharmaceutically acceptable salt thereof.

6. The method for treating an allergic disease of claim 5, wherein the allergic disease is asthma.

7. The method for treating an allergic disease of claim 5, wherein the allergic disease is atopic dermatitis.

* * * * *

UNITED STATES PATENT AND TRADEMARK OFFICE
CERTIFICATE OF CORRECTION

PATENT NO. : 6,197,774 B1 Page 1 of 1
DATED : March 6, 2001
INVENTOR(S) : Satoshi Yamada et al.

It is certified that error appears in the above-identified patent and that said Letters Patent is hereby corrected as shown below:

<u>Column 42,</u>
Line 5,

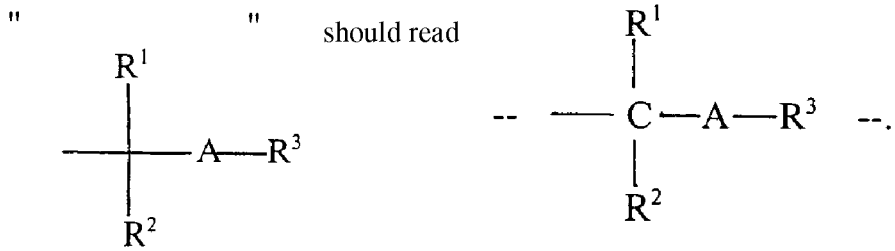

Signed and Sealed this

Eighth Day of July, 2003

JAMES E. ROGAN
*Director of the United States Patent and Trademark Office*